US012758504B2

(12) United States Patent
Geho

(10) Patent No.: US 12,758,504 B2
(45) Date of Patent: Oct. 13, 2026

(54) COMPOSITIONS COMPRISING LIPID-BASED NANOPARTICLES FOR TREATING DIABETES MELLITUS

(71) Applicant: SDG, Inc., Cleveland, OH (US)

(72) Inventor: W. Blair Geho, Wooster, OH (US)

(73) Assignee: Diasome Pharmaceuticals, Inc., Cleveland, OH (US)

( * ) Notice: Subject to any disclaimer, the term of this patent is extended or adjusted under 35 U.S.C. 154(b) by 506 days.

(21) Appl. No.: 18/307,459

(22) Filed: Apr. 26, 2023

(65) Prior Publication Data

US 2024/0108585 A1 Apr. 4, 2024

Related U.S. Application Data

(63) Continuation of application No. 16/959,617, filed as application No. PCT/US2019/012557 on Jan. 7, 2019, now abandoned.

(60) Provisional application No. 62/614,109, filed on Jan. 5, 2018.

(51) Int. Cl.

| | |
|---|---|
| ***A61K 9/51*** | (2006.01) |
| ***A61K 38/28*** | (2006.01) |
| ***A61P 3/10*** | (2006.01) |
| ***B82Y 5/00*** | (2011.01) |

(52) U.S. Cl.

CPC ............ *A61K 9/5123* (2013.01); *A61K 38/28* (2013.01); *A61P 3/10* (2018.01); *B82Y 5/00* (2013.01)

(58) Field of Classification Search

CPC ......... A61K 9/5123; A61K 38/28; A61P 3/10; B82Y 5/00

See application file for complete search history.

(56) References Cited

U.S. PATENT DOCUMENTS

| | | | | |
|---|---|---|---|---|
| 4,501,728 | A | | 2/1985 | Geho et al. |
| 4,522,803 | A | | 6/1985 | Lenk et al. |
| 4,603,044 | A | * | 7/1986 | Geho ..................... A61Q 11/00 424/9.37 |
| 4,740,375 | A | | 4/1988 | Geho et al. |
| 4,762,915 | A | | 8/1988 | Kung et al. |
| 4,863,896 | A | | 9/1989 | Geho et al. |
| 4,946,787 | A | | 8/1990 | Eppstein et al. |
| 5,000,960 | A | | 3/1991 | Wallach et al. |
| 5,019,369 | A | | 5/1991 | Presant et al. |
| 5,059,421 | A | | 10/1991 | Loughrey et al. |
| 5,104,661 | A | | 4/1992 | Lau |
| 5,120,710 | A | | 6/1992 | Liedtke et al. |
| 5,376,380 | A | | 12/1994 | Kikuchi et al. |
| 5,399,331 | A | | 3/1995 | Loughrey et al. |
| 5,411,730 | A | | 5/1995 | Kirpotin et al. |
| 5,420,108 | A | | 5/1995 | Shohet |
| 5,514,670 | A | | 5/1996 | Friedman et al. |
| 5,567,432 | A | | 10/1996 | Lau et al. |
| 5,690,907 | A | | 11/1997 | Lanza et al. |
| 5,795,895 | A | | 8/1998 | Anchors |
| 5,968,972 | A | | 10/1999 | Broder et al. |
| 6,004,583 | A | | 12/1999 | Plate et al. |
| 6,063,400 | A | | 5/2000 | Geho et al. |
| 6,077,834 | A | | 6/2000 | Cheng |
| 6,177,099 | B1 | | 1/2001 | Lau et al. |
| 6,207,185 | B1 | | 3/2001 | See et al. |
| 6,365,156 | B1 | | 4/2002 | Lee |
| 6,573,101 | B1 | | 6/2003 | Goomer |
| 6,692,766 | B1 | | 2/2004 | Rubinstein et al. |
| 6,726,924 | B2 | | 4/2004 | Keller |
| 7,169,410 | B1 | | 1/2007 | Lau et al. |
| 7,192,605 | B2 | | 3/2007 | Herweijer et al. |
| 7,858,116 | B2 | | 12/2010 | Lau et al. |
| 7,871,641 | B2 | | 1/2011 | Lau et al. |
| 8,846,053 | B2 | | 9/2014 | Geho et al. |
| 8,962,015 | B2 | | 2/2015 | Lau et al. |
| 9,034,372 | B2 | | 5/2015 | Lau et al. |
| 9,145,453 | B2 | | 9/2015 | Geho et al. |
| 9,943,602 | B2 | | 4/2018 | Geho et al. |
| 10,004,686 | B2 | | 6/2018 | Lau et al. |
| 10,463,616 | B2 | | 11/2019 | Lau et al. |
| 10,568,835 | B2 | | 2/2020 | Lau et al. |
| 10,751,418 | B2 | | 8/2020 | Geho et al. |
| 10,918,700 | B2 | | 2/2021 | Geho |
| 11,071,715 | B2 | | 7/2021 | Geho |
| 11,077,173 | B2 | | 8/2021 | Geho |
| 11,517,529 | B2 | | 12/2022 | Lau et al. |
| 2002/0039595 | A1 | | 4/2002 | Keller et al. |
| 2002/0061331 | A1 | | 5/2002 | Zasadzinski et al. |

(Continued)

FOREIGN PATENT DOCUMENTS

| | | | |
|---|---|---|---|
| CA | 2431212 | A1 | 7/2002 |
| CA | 2519249 | A | 3/2004 |

(Continued)

OTHER PUBLICATIONS

Lee et al.; Tetraiodothyroacetic acid-tagged liposomes for enhanced delivery of anticancer drug to tumor tissue via integrin receptor; Elsevier; Journal of Controlled Release 164 (2012) 213-220 (Year: 2012).*

Liu et al.; Solid lipid nanoparticles for pulmonary delivery of insulin; Elsevier; International Journal of Pharmaceutics 356 (2008) 333-344 (Year: 2008).*

Bolus vs basal—Google Search (Year: 2025).*

Distearoyl lecithin (dsl) synonym—Google Search (Year: 2025).*

Neumann; The Metabolic Effects of Leptin Therapy and Glucagon Suppression Therapy in Mouse Models of Diabetes; The University of British Columbia; Doctor of Philosophy Thesis; 2017. (Year: 2017).*

Diabetes mellitus—Google Search (Year: 2025).*

Hba1c levels—Google Search (Year: 2025).*

Stearoyl lysophosphatidylcholine—Google Search (Year: 2025).*

Is biotin metabolized by the liver—Google Search (Year: 2025).*

(Continued)

*Primary Examiner* — Robert A Wax

*Assistant Examiner* — John W Lippert, III

(74) *Attorney, Agent, or Firm* — Saul Ewing LLP; Kathryn Doyle; Domingos J. Silva

(57) ABSTRACT

The invention provides methods of treating a subject having diabetes mellitus. The invention further provides methods of increasing distribution volume of insulin in a subject.

33 Claims, 10 Drawing Sheets

(56) References Cited

U.S. PATENT DOCUMENTS

| | | | | |
|---|---|---|---|---|
| 2003/0133972 | A1 | 7/2003 | Danthi et al. | |
| 2004/0016035 | A1 | 1/2004 | Floyd | |
| 2004/0033256 | A1 | 2/2004 | Margalit et al. | |
| 2004/0180147 | A1 | 9/2004 | Parikh et al. | |
| 2004/0265367 | A1 | 12/2004 | Thorpe et al. | |
| 2005/0008688 | A1 | 1/2005 | Betageri et al. | |
| 2005/0026826 | A1 | 2/2005 | Hoenig | |
| 2005/0049179 | A1 | 3/2005 | Davidson et al. | |
| 2005/0059100 | A1 | 3/2005 | Meares et al. | |
| 2005/0123600 | A1 | 6/2005 | Trubetskoy et al. | |
| 2005/0175541 | A1 | 8/2005 | Lanza et al. | |
| 2005/0202075 | A1 | 9/2005 | Pardridge et al. | |
| 2006/0008461 | A1 | 1/2006 | Yatvin et al. | |
| 2006/0009381 | A1 | 1/2006 | Reutelingsperger | |
| 2006/0141047 | A1 | 6/2006 | Heller et al. | |
| 2006/0222697 | A1 | 10/2006 | Lau et al. | |
| 2006/0222698 | A1 | 10/2006 | Lau et al. | |
| 2007/0104777 | A1 | 5/2007 | Lau et al. | |
| 2007/0218117 | A1 | 9/2007 | Lau et al. | |
| 2007/0281325 | A1 | 12/2007 | Danielzadeh | |
| 2008/0014255 | A1 | 1/2008 | Tagawa et al. | |
| 2008/0050372 | A1 | 2/2008 | Grunberger et al. | |
| 2008/0207490 | A1 | 8/2008 | Yea et al. | |
| 2008/0279815 | A1 | 11/2008 | Cevc | |
| 2008/0305156 | A1 | 12/2008 | Laing et al. | |
| 2009/0087479 | A1 | 4/2009 | Lau et al. | |
| 2009/0123530 | A1 | 5/2009 | Betageri et al. | |
| 2009/0185976 | A1 | 7/2009 | See et al. | |
| 2010/0129428 | A1 | 5/2010 | Lau et al. | |
| 2011/0027209 | A1 | 2/2011 | Anzali et al. | |
| 2011/0135725 | A1 | 6/2011 | Lau et al. | |
| 2011/0195988 | A1 | 8/2011 | Alan March | |
| 2012/0035105 | A1 | 2/2012 | Geho et al. | |
| 2012/0231069 | A1 | 9/2012 | Nowotnik et al. | |
| 2013/0017239 | A1 | 1/2013 | Viladot Petit et al. | |
| 2013/0183270 | A1 | 7/2013 | Geho et al. | |
| 2014/0243430 | A1* | 8/2014 | Geho | A23L 33/10 514/784 |
| 2015/0031608 | A1 | 1/2015 | Lau et al. | |
| 2015/0125518 | A1 | 5/2015 | Lau et al. | |
| 2015/0190476 | A1* | 7/2015 | Schobel | B82Y 5/00 514/11.7 |
| 2015/0224054 | A1 | 8/2015 | Bell et al. | |
| 2016/0022711 | A1 | 1/2016 | Choung et al. | |
| 2016/0168199 | A1 | 6/2016 | Brines et al. | |
| 2016/0367677 | A1 | 12/2016 | Stoilova-Mcphie | |
| 2017/0319573 | A1 | 11/2017 | Drummond et al. | |
| 2018/0000953 | A1 | 1/2018 | Almarsson et al. | |
| 2018/0110771 | A1 | 4/2018 | Drummond et al. | |
| 2023/0172868 | A1 | 6/2023 | Geho | |

FOREIGN PATENT DOCUMENTS

| | | | | |
|---|---|---|---|---|
| CN | 1274605 | A | 11/2000 | |
| CN | 1895224 | A | 1/2007 | |
| CN | 102014880 | A | 4/2011 | |
| EP | 0577146 | A2 | 1/1994 | |
| EP | 2205217 | B1 | 12/2017 | |
| JP | H05239 | A | 1/1993 | |
| JP | H11116478 | A | 4/1999 | |
| JP | 2007525433 | A | 9/2007 | |
| JP | 2010540559 | A | 12/2010 | |
| KR | 20080043742 | A | 5/2008 | |
| WO | 8503640 | A1 | 8/1985 | |
| WO | 8701587 | A1 | 3/1987 | |
| WO | 8800474 | A1 | 1/1988 | |
| WO | 9610585 | A1 | 4/1996 | |
| WO | 9617596 | A1 | 6/1996 | |
| WO | 9959545 | A1 | 11/1999 | |
| WO | 0032167 | A1 | 6/2000 | |
| WO | 2006127361 | A2 | 11/2006 | |
| WO | 2009042945 | A1 | 4/2009 | |
| WO | 2009135190 | A1 | 11/2009 | |
| WO | 2010111271 | A1 | 9/2010 | |
| WO | 2011119953 | A1 | 9/2011 | |
| WO | WO-2015081096 | A2 * | 6/2015 | A61K 47/68 |
| WO | 2016118724 | A1 | 7/2016 | |
| WO | 2018169954 | A1 | 9/2018 | |
| WO | 2019136386 | A1 | 7/2019 | |

OTHER PUBLICATIONS

Kumar, et al., "Lysophosphatidylcholine stabilizes small unilamellar phosphatidylcholine vesicles: Phosphorus-3 1 NMR evidence for the "wedge" effect", Biophys J, vol. 55, Apr. 1989, pp. 789-792.
Ansell, et al., "3-(2-Pyridyldithio)propionic Acid Hydrazide as a Cross-Linker in the Formation of Liposome-Antibody Conjugates", Bioconjugate Chem, vol. 7, No. 4, Jul. 1996., pp. 490-496.
Ansell, et al., "Antibody Conjugation Methods for Active Targeting of Liposomes", Methods in Molecular Medicine, vol. 25: Drug Targeting: Strategies, Principles and Applications, 2000, pp. 51-67.
Cantenys, et al., "Covalent Attachment of Insulin to the Outer Surface of Liposomes", Biochem Biophys Res Comm, vol. 117, No. 2, Dec. 1983, pp. 399-405.
Dong, C., et al., "Acacia-Gelatin Microencapsulated Liposomes: Preparation, Stability, and Release of Acetylsalicylic Acid", Pharmaceutical Research, vol. 10, No. 1,, 1993, pp. 141-146.
Erion, et al., "Targeting Thyroid hormone receptor-beta agonists to the liver reduces cholesterol and triglycerides and improves the therapeutic index", PNAS, vol. 104, No. 39, Sep. 25, 2007, pp. 15490-15495.
Geho, et al., "Hepatic-Directed Vesicle Insulin: A Review of Formulation Development and Preclinical Evaluation", J Diabetes Sci Technol, vol. 3, Issue 6, Nov. 2009, pp. 1451-1459.
Hermanson, "Heterobifunctional Crosslinkers", Bioconjugate Techniques, 2nd Edition, 2008, pp. 276-335 & 878-881 & 884-887 & 895-899.
Israelachvili, et al., "Physical principles of membrane organization", Quarterly Reviews of Biophysics, vol. 13, No. 2, 1980, pp. 121-200.
Iwanaga, et al., "Oral Delivery of Insulin by Using Surface Coating Liposomes Improvement of Stability of Insulin in GI Tract", Intl J Pharm, vol. 157, 1997, pp. 73-80.
Manjappa, et al., "Antibody Derivation and Conjugation Strategies: Application in Preparation of Stealth Immunoliposome to Target chemotherapeutics to Tumor", J Controlled Rel, vol. 150, No. 1, Oct. 2010, pp. 2-22.
Soga, et al., "Lysophosphatidylcholine enhances glucose-dependent insulin secretion via an orphan G-protein-coupled receptor", Biochem Biophys Res Comm, vol. 326, 2005, pp. 744-751.
Takeoka, et al., "Rolling Properties of rGPlbalpha-conjugated phospholipid vesicles with different membrane flexibilities on vWf surface under flow conditions", Biochem Biophys Res Comm, vol. 296, Jul. 2002, pp. 765-770.
Vesely, D.L. , et al., "Isolation of a Biotin Receptor From Hepatic Plasma Membranes", Biochemical and Biophysical Research Communications, vol. 143, No. 3, 1987, pp. 913-916.
Walde, et al., "Enzymes inside lipid vesicles: preparation, reactivity and applications", Biomolecular Engineering, vol. 18, 2001, pp. 143-177.
Zhang, et al., "Biotinylated liposomes as potential carriers for the oral delivery of insulin", Nanomedicine: Nanotechnology, Biology, and Medicine, vol. 10, 2014, pp. 167-176.
International Search Report & Written Opinion dated Mar. 15, 2019 for corresponding PCT Application No. PCT/US2019/012557.
Bode, et al., "Comparison of Insulin Aspart with Buffered Regular Insulin and Insulin Lispro in Continuous Subcutaneous Insulin Infusion", Diabetes Care, vol. 25, No. 3, Mar. 2002, pp. 439-444.
Hirsh, I., "Insulin Analogues", N Engl J Med, vol. 352, No. 2, Jan. 13, 2005, pp. 174-183.
Kitagawa, et al., "Properties of Liposomal Membranes Containing Lysolecithin", J Biochem, vol. 79, 1976, pp. 1123-1133.
Extended European Search Report dated Dec. 3, 2020 for related EP Application 18 766 906.4.

(56) References Cited

OTHER PUBLICATIONS

Grigoras, A.G., "Polymer-lipid hybrid systems used as carriers for insulin delivery", Nanomedicine, Nanotechnology, Biology and Medicine, vol. 13, No. 8, 2017, pp. 2425-2437.
Vesely, D. L., et al in BBRC, vol. 143, #3, pp. 913-916, 1987.
Ebihara, et al., "Effect of Benzyl Alcohol on Lipid Bilayers—A Comparison of Bilayer Systems", Biophys J, vol. 28, 1979, pp. 185-196.
Paiva, et al., "m-Cresol affects the lipid bilayer in membrane models and living neurons", RSC Adv, vol. 6, 2016, pp. 105699-105712.
Usami, et al., "Effects of Phenol and Related Compounds on Erythrocytes and Hepatocytes from Rats and Dipalmitoyl Phosphatidylcholine-Liposomes", Folia Pharmacologica Japonica, 89(4), 1987, pp. 235-241.
Geho, et al., "A Single-blind, Placebo-controlled, Dose-ranging Trial of Oral Hepatic-directed Vesicle Insulin Add-on to Oral Antidiabetic Treatment in Patients with Type 2 Diabetes Mellitus", J Diabetes Sci Technol, vol. 8, No. 3, 2014, pp. 551-559.

* cited by examiner

| Time (Min) | HDV AUC Reduction |
|---|---|
| 0-15 | -96% |
| 0-30 | -66% |
| 0-60 | -30% |
| 0-90 | -12% |
| 0-120 | -1% |

COMPOSITIONS COMPRISING LIPID-BASED NANOPARTICLES FOR TREATING DIABETES MELLITUS

CROSS-REFERENCE TO RELATED APPLICATIONS

The present application is a continuation of, and claims priority to, U.S. patent application Ser. No. 16/959,617 filed Jul. 1, 2020, which is a 35 U.S.C. § 371 national phase application of, and claims priority to, International Application No. PCT/US2019/012557, filed Jan. 7, 2019, which claims priority pursuant to 35 U.S.C. § 119(e) to U.S. Provisional Patent Application No. 62/614,109, filed Jan. 5, 2018, all of which applications are incorporated herein by reference in their entireties.

BACKGROUND OF THE INVENTION

Phospholipid nanoparticles of diameter lower than about 100 nm are often used as carriers to improve in vivo delivery of active pharmaceutical ingredients (APIs), such as peptides and biogenic amines. The nanoparticles' small particle size allows them to easily cross membrane barriers. Further, nanoparticles may provide rapid and specific delivery of APIs to desired cell surface receptors, resulting in improved pharmacological action and need for lower API doses. The targeted API delivery also leads to lower toxicity, because of the API's reduced delivery to unwanted tissues in the body.

An example of such nanoparticles is the hepatic delivery vesicle (HDV), which comprises a hepatocyte-targeting component and delivers APIs to hepatocyte receptors. In contrast, nanoparticles without a hepatocyte-targeting components generally accumulate in liver macrophages called Kupffer cells, along with other macrophage cells in the body.

Diabetes mellitus, encompassing Type 1 and Type 21 forms, is a disorder affecting large numbers of people worldwide. Diabetes mellitus management comprises normalizing blood glucose levels in the subject, and that may require multiple daily injections of an insulin-based product. Despite the presence of various insulin-based products on the market, there is still a need for novel insulin-containing formulations that control glucose blood levels in the subject over a wide period of time.

Certain medications approved for insulin-requiring diabetes mellitus treatment comprise an insulin analog that is to be administered subcutaneously, often as a time-release formulation. Because of the abundance of insulin receptors in peripheral adipose and muscle tissues, such administration releases the insulin analog to peripheral tissues, but generally not to the liver. In one aspect, proper insulin-requiring diabetes mellitus treatment requires an insulin-based formulation in which a portion of the dosed insulin is released to peripheral tissues throughout the day and another portion of the dosed insulin is targeted for liver delivery. Such need extends as well to other therapeutic agents for which targeted liver delivery has advantageous therapeutic and/or pharmacological properties.

There is thus an unmet need in the art for compositions and methods for administering insulin to a subject, such that the insulin is delivered to peripheral tissues as well as to the liver of the subject. Such compositions and methods can be used to manage blood glucose levels in Type 1 and Type 2 diabetic patients. The present invention meets this need.

BRIEF SUMMARY OF THE INVENTION

The present invention provides a method of treating a subject having diabetes mellitus. The present invention further provides a method of increasing the volume of distribution of an insulin administered to a subject. The present invention further provides a method of increasing or improving glycemic control in a subject being administered an insulin. The present invention further provides a method of increasing or improving basal glucose control in a subject being administered an insulin. The present invention further provides a method of increasing or improving basal glucose control in a subject being administered an insulin.

In certain embodiments, the method comprises administering to the subject a composition comprising a lipid-based nanoparticle, wherein the insulin is dispersed within the nanoparticle.

In certain embodiments, the method comprises administering in a continuous manner to the subject a composition comprising a lipid-based nanoparticle, wherein the insulin is dispersed within the nanoparticle.

In certain embodiments, the amount of the insulin in the composition is lower than the amount of free insulin that would be administered to treat the diabetes mellitus in the subject.

In certain embodiments, the administration of the composition results in approximately equivalent or better blood glucose control as afforded by the amount of free insulin that would be administered to treat the diabetes mellitus in subject.

In certain embodiments, the administration of the composition does not cause significant hypoglycemia in the subject;

In certain embodiments, the nanoparticle is enclosed by a bipolar lipid membrane comprising cholesterol, dicetyl phosphate, an amphipathic lipid, and a hepatocyte receptor binding molecule.

In certain embodiments, the amphipathic lipid comprises at least one selected from the group consisting of 1,2-distearoyl-sn-glycero-3-phosphocholine, 1,2-dipalmitoyl-sn-glycerol-[3-phospho-rac-(1-glycerol)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine.

In certain embodiments, the at least one hepatocyte receptor binding molecule extends outward from the nanoparticle.

In certain embodiments, the size of the nanoparticle ranges from about 10 nm to about 150 nm.

In certain embodiments, the amount of the insulin in the composition causes no significant iatrogenic hyperinsulinemia in the subject.

In certain embodiments, the amount of free insulin that would be administered to treat the diabetes mellitus in subject causes significant iatrogenic hyperinsulinemia in the subject.

In certain embodiments, the insulin comprises bolus insulin.

In certain embodiments, the subject is further administered a basal insulin.

In certain embodiments, the basal insulin is formulated in a composition comprising a lipid-based nanoparticle of the invention.

In certain embodiments, the composition is administered continuously to the subject over a period of at least 24 hours.

In certain embodiments, the composition is administered continuously to the subject using a pump, or equivalent delivery equipment.

In certain embodiments, the subject has a hemoglobin A1c level equal to or greater than about 10%. In certain embodiments, the subject has a hemoglobin A1c level equal to or greater than about 9.9%. In certain embodiments, the subject has a hemoglobin A1c level equal to or greater than about 9.8%. In certain embodiments, the subject has a hemoglobin A1c level equal to or greater than about 9.7%. In certain embodiments, the subject has a hemoglobin A1c level equal to or greater than about 9.6%. In certain embodiments, the subject has a hemoglobin A1c level equal to or greater than about 9.5%. In certain embodiments, the subject has a hemoglobin A1c level equal to or greater than about 9.4%. In certain embodiments, the subject has a hemoglobin A1c level equal to or greater than about 9.3%. In certain embodiments, the subject has a hemoglobin A1c level equal to or greater than about 9.2%. In certain embodiments, the subject has a hemoglobin A1c level equal to or greater than about 9.1%. In certain embodiments, the subject has a hemoglobin A1c level equal to or greater than about 9.0%. In certain embodiments, the subject has a hemoglobin A1c level equal to or greater than about 8.9%. In certain embodiments, the subject has a hemoglobin A1c level equal to or greater than about 8.8%. In certain embodiments, the subject has a hemoglobin A1c level equal to or greater than about 8.7%. In certain embodiments, the subject has a hemoglobin A1c level equal to or greater than about 8.6%. In certain embodiments, the subject has a hemoglobin A1c level equal to or greater than about 8.5%. In certain embodiments, the subject has a hemoglobin A1c level equal to or greater than about 8.4%. In certain embodiments, the subject has a hemoglobin A1c level equal to or greater than about 8.3%. In certain embodiments, the subject has a hemoglobin A1c level equal to or greater than about 8.2%. In certain embodiments, the subject has a hemoglobin A1c level equal to or greater than about 8.1%. In certain embodiments, the subject has a hemoglobin A1c level equal to or greater than about 8.0%. In certain embodiments, the subject has a hemoglobin A1c level equal to or greater than about 7.9%. In certain embodiments, the subject has a hemoglobin A1c level equal to or greater than about 7.8%. In certain embodiments, the subject has a hemoglobin A1c level equal to or greater than about 7.7%. In certain embodiments, the subject has a hemoglobin A1c level equal to or greater than about 7.6%. In certain embodiments, the subject has a hemoglobin A1c level equal to or greater than about 7.5%. In certain embodiments, the subject has a hemoglobin A1c level equal to or greater than about 7.4%. In certain embodiments, the subject has a hemoglobin A1c level equal to or greater than about 7.3%. In certain embodiments, the subject has a hemoglobin A1c level equal to or greater than about 7.2%. In certain embodiments, the subject has a hemoglobin A1c level equal to or greater than about 7.1%. In certain embodiments, the subject has a hemoglobin A1c level equal to or greater than about 7.0%. In certain embodiments, the subject has a hemoglobin A1c level equal to or greater than about 6.9%. In certain embodiments, the subject has a hemoglobin A1c level equal to or greater than about 6.8%. In certain embodiments, the subject has a hemoglobin A1c level equal to or greater than about 6.7%. In certain embodiments, the subject has a hemoglobin A1c level equal to or greater than about 6.6%. In certain embodiments, the subject has a hemoglobin A1C level equal to or greater than about 6.5%.

In certain embodiments, the subject has a hemoglobin A1c level equal to or lower than about 10%. In certain embodiments, the subject has a hemoglobin A1c level equal to or lower than about 9.9%. In certain embodiments, the subject has a hemoglobin A1c level equal to or lower than about 9.8%. In certain embodiments, the subject has a hemoglobin A1c level equal to or lower than about 9.7%. In certain embodiments, the subject has a hemoglobin A1c level equal to or lower than about 9.6%. In certain embodiments, the subject has a hemoglobin A1c level equal to or lower than about 9.5%. In certain embodiments, the subject has a hemoglobin A1c level equal to or lower than about 9.4%. In certain embodiments, the subject has a hemoglobin A1c level equal to or lower than about 9.3%. In certain embodiments, the subject has a hemoglobin A1c level equal to or lower than about 9.2%. In certain embodiments, the subject has a hemoglobin A1c level equal to or lower than about 9.1%. In certain embodiments, the subject has a hemoglobin A1c level equal to or lower than about 9.0%. In certain embodiments, the subject has a hemoglobin A1c level equal to or lower than about 8.9%. In certain embodiments, the subject has a hemoglobin A1c level equal to or lower than about 8.8%. In certain embodiments, the subject has a hemoglobin A1c level equal to or lower than about 8.7%. In certain embodiments, the subject has a hemoglobin A1c level equal to or lower than about 8.6%. In certain embodiments, the subject has a hemoglobin A1c level equal to or lower than about 8.5%. In certain embodiments, the subject has a hemoglobin A1c level equal to or lower than about 8.4%. In certain embodiments, the subject has a hemoglobin A1c level equal to or lower than about 8.3%. In certain embodiments, the subject has a hemoglobin A1c level equal to or lower than about 8.2%. In certain embodiments, the subject has a hemoglobin A1c level equal to or lower than about 8.1%. In certain embodiments, the subject has a hemoglobin A1c level equal to or lower than about 8.0%. In certain embodiments, the subject has a hemoglobin A1c level equal to or lower than about 7.9%. In certain embodiments, the subject has a hemoglobin A1c level equal to or lower than about 7.8%. In certain embodiments, the subject has a hemoglobin A1c level equal to or lower than about 7.7%. In certain embodiments, the subject has a hemoglobin A1c level equal to or lower than about 7.6%. In certain embodiments, the subject has a hemoglobin A1c level equal to or lower than about 7.5%. In certain embodiments, the subject has a hemoglobin A1c level equal to or lower than about 7.4%. In certain embodiments, the subject has a hemoglobin A1c level equal to or lower than about 7.3%. In certain embodiments, the subject has a hemoglobin A1c level equal to or lower than about 7.2%. In certain embodiments, the subject has a hemoglobin A1c level equal to or lower than about 7.1%. In certain embodiments, the subject has a hemoglobin A1c level equal to or lower than about 7.0%. In certain embodiments, the subject has a hemoglobin A1c level equal to or lower than about 6.9%. In certain embodiments, the subject has a hemoglobin A1c level equal to or lower than about 6.8%. In certain embodiments, the subject has a hemoglobin A1c level equal to or lower than about 6.7%. In certain embodiments, the subject has a hemoglobin A1c level equal to or lower than about 6.6%. In certain embodiments, the subject has a hemoglobin A1C level equal to or greater than about 6.5%.

In certain embodiments, the membrane further comprises at least one agent selected from the group consisting of a stabilizer and stearoyl lysophosphatidylcholine. In certain embodiments, the stabilizer is selected from the group consisting of m-cresol, benzyl alcohol, methyl 4-hydroxybenzoate, thiomersal, and butylated hydroxytoluene (2,6-di-tert-butyl-4-methylphenol). In certain embodiments, the stabilizer ranges from about 10% to about 25% (w/w) in the membrane. In certain embodiments, the stearoyl lysophosphatidylcholine ranges from about 5% to about 30% (w/w) in the membrane.

In certain embodiments, the insulin is covalently bound to the nanoparticle.

In certain embodiments, the insulin is not covalently bound to the nanoparticle.

In certain embodiments, the insulin is suspended in an aqueous solution comprising a free dissolved insulin that is not dispersed within the nanoparticle.

In certain embodiments, the nanoparticle-dispersed insulin is selected from the group consisting of insulin lispro, insulin aspart, regular insulin, insulin glargine, insulin zinc, extended human insulin zinc suspension, isophane insulin, human buffered regular insulin, insulin glulisine, recombinant human regular insulin, recombinant human insulin isophane, and any combinations thereof.

In certain embodiments, the free dissolved insulin is selected from the group consisting of insulin lispro, insulin aspart, regular insulin, insulin glargine, insulin zinc, extended human insulin zinc suspension, isophane insulin, human buffered regular insulin, insulin glulisine, recombinant human regular insulin, recombinant human insulin isophane, and any combinations thereof.

In certain embodiments, the amphipathic lipid comprises at least one selected from the group consisting of 1,2-distearoyl-sn-glycero-3-phosphocholine, 1,2-dipalmitoyl-sn-glycero-3-phosphocholine, 1,2-dipalmitoyl-sn-glycero-3-[phospho-rac-(1-glycerol)], 1,2-distearoyl-sn-glycero-3-phosphoethanolamine, and 1,2-dipalmitoyl-sn-glycero-3-phosphoethanolamine-N-(succinyl).

In certain embodiments, the hepatocyte receptor binding molecule comprises biotin. In certain embodiments, the biotin-containing hepatocyte receptor binding molecule comprises at least one selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE (2,3-diacetoxypropyl 2-(5-((3aS,6aR)-2-oxohexahydro-1H-thieno[3,4-d]imidazol-4-yl)pentanamido)ethyl phosphate); biotin-X-DHPE (2,3-diacetoxypropyl 2-(6-(5-((3aS,6aR)-2-oxohexahydro-1H-thieno[3,4-d]imidazol-4-yl)pentanamido)hexanamido) ethyl phosphate); 12-((biotinyl)amino) dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol) amine; (+) biotin 4-amidobenzoic acid sodium salt; Biotin 2-N-acetylamino-2-deoxy-f3-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; and biotin 6-O-phospho-α-D-mannopyranoside. In certain embodiments, the biotin-containing hepatocyte receptor binding molecule comprises at least one selected from the group consisting of biotin DHPE and biotin-X-DHPE.

In certain embodiments, the composition further comprises cellulose acetate phthalate, which is at least partially bound to the therapeutic agent dispersed within the nanoparticle.

In certain embodiments, the composition further comprises at least one charged organic molecule bound to the therapeutic agent dispersed within the nanoparticle, wherein the charged organic molecule is at least one selected from the group consisting of protamines, polylysine, poly(arg-pro-thr), in a mole ratio of 1:1:1, poly(DL-Ala-poly-L-lys), in a mole ratio of 6:1, histones, sugar polymers comprising a primary amino group, polynucleotides with primary amino groups, proteins comprising amino acid residues with carboxyl ($COO^-$) or sulfhydral ($S^-$) functional groups, and acidic polymers.

In certain embodiments, the cholesterol ranges from about 5% to about 25% (w/w) in the membrane. In certain embodiments, the dicetyl phosphate ranges from about 10% to about 25% (w/w) in the membrane. In certain embodiments, the DSPC ranges from about 40% to about 75% (w/w) in the membrane. In certain embodiments, the hepatocyte receptor binding molecule ranges from about 0.5% to about 10% (w/w) in the membrane. In certain embodiments, the amount of the stearoyl lysophosphatidylcholine in the membrane is about 5%-30% (w/w) of the amount of DSPC in the membrane.

In certain embodiments, the membrane comprises cholesterol, dicetyl phosphate, DSPC, stearoyl lysophosphatidylcholine, m-cresol, and at least one selected from the group consisting of biotin DHPE and biotin-X-DHPE.

In certain embodiments, the membrane comprises cholesterol, dicetyl phosphate, DSPC, m-cresol, and at least one selected from the group consisting of biotin DHPE and biotin-X-DHPE.

In certain embodiments, the membrane comprises cholesterol, dicetyl phosphate, DSPC, stearoyl lysophosphatidylcholine, and at least one selected from the group consisting of biotin DHPE and biotin-X-DHPE.

In certain embodiments, the membrane comprises cholesterol, dicetyl phosphate, DSPC, stearoyl lysophosphatidylcholine, m-cresol, and biotin DHPE in a % (w/w) ratio of about 9.4:18.1:56.8:14.1:0.0:1.5.

In certain embodiments, the membrane comprises cholesterol, dicetyl phosphate, DSPC, stearoyl lysophosphatidylcholine, m-cresol, and biotin DHPE in a % (w/w) ratio of about 7.7:15.0:58.6:0.0:17.4:1.3.

In certain embodiments, the membrane comprises cholesterol, dicetyl phosphate, DSPC, stearoyl lysophosphatidylcholine, m-cresol, and biotin DHPE in a % (w/w) ratio of about 8.4:16.2:47.5:7.6:19.0:1.3.

In certain embodiments, the subject has diabetes mellitus.

In certain embodiments, the subject has Type 1 diabetes or Type 2 diabetes.

BRIEF DESCRIPTION OF THE DRAWINGS

For the purposes of illustrating the invention, there are depicted in the drawings certain embodiments of the invention. However, the invention is not limited to the precise arrangements and instrumentalities of the embodiments depicted in the drawings.

FIG. 2A illustrates mean daily glucose values (absolute values over two weeks). FIG. 2B illustrates two-week absolute change in mean nighttime glucose (mg/dL). FIG. 2C illustrates mixed meal tolerance test changes from baseline blood glucose.

FIG. 3A illustrates time in ranges by continuous glucose monitoring (CGM), in terms of mean % change from week 1 to weeks 6-7. FIG. 3B illustrates HDV lispro effect on hypoglycemia, in terms of mean % change in glucose AUC below 70 mg/dL and 54 mg/dL. FIG. 3C illustrates differences in mean blood glucose values during weeks 6-7.

DETAILED DESCRIPTION OF THE INVENTION

Figure 1A:
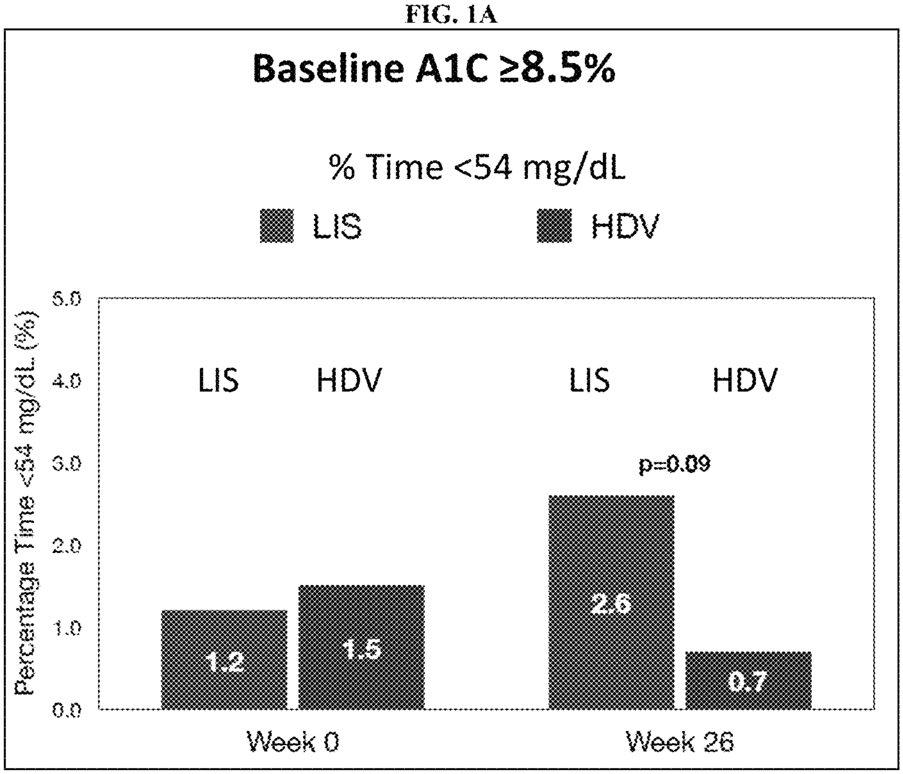
FIGS. 1A-1F illustrate changes in hypoglycemia, A1c, and insulin by baseline A1c. p-Values indicate significance of between-group differences at endpoint.

The invention relates in part to the unexpected discovery that administration of insulin dispersed within certain lipid-based nanoparticles allows for an increase (or improvement) in volume of distribution of the insulin. The invention further relates in part to the unexpected discovery that the administration dose of insulin dispersed within certain lipid-based nanoparticles should be adjusted so as to treat the diabetes mellitus without cause hypoglycemia in the subject.

In certain embodiments, the use of the HDV-insulin potentiates the effect on insulin in the subject, allowing for use of lower amounts of insulin and thus avoiding iatrogenic hyperinsulinemia and/or hypoglycemia in the subject.

In certain embodiments, the use of the HDV-insulin allows for use of lower amounts of insulin, and thus reduce or eliminates side effects associated with hyperinsulinemia (which can be derived from use of large amounts of insulin), such as but not limited to hypoglycemia, increased risk of polycystic ovary syndrome (PCOS), increased synthesis of VLDL (hypertriglyceridemia), hypertension (insulin increases sodium retention by the renal tubules), coronary artery disease (increased insulin damages endothelial cells), increased risk of cardiovascular disease, and/or weight gain and lethargy.

Without wishing to be limited by any theory, the standard treatment of a diabetic subject involves a 50:50 ratio of administered bolus insulin and basal insulin. Using HDV in at least the bolus insulin allows for an insulin ratio that is closer to physiological levels (such as, for example, using lower basal insulin amounts).

In certain embodiments, the nanoparticles useful within the invention are described in U.S. Patent Application Nos. US20110135725 and US20090087479 and PCT Patent Application Publication No. WO 2018/169954, all of which are incorporated herein in their entireties by reference. In certain embodiments, the reduced or minimal aggregation properties of the nanoparticle of the invention improves its stability and pharmaceutical developability as compared to nanoparticles of the prior art.

In certain embodiments, the lipid-based nanoparticle of the invention is defined and/or enclosed by a bipolar lipid membrane. In other embodiments, the nanoparticle of the invention comprises a hepatocyte-targeting compound, which helps deliver the therapeutic agent (such as, but not limited to, insulin) associated with, and/or dispersed within, the nanoparticle to a hepatocyte. In yet other embodiments, the nanoparticle of the invention is part of a composition further comprising a "free" therapeutic agent, which is not associated with, and/or dispersed within, the nanoparticle. The nanoparticle, and any compositions comprising the same, can be administered by any compatible and/or feasible routes, such as but not limited to by injection (such as, for example, subcutaneously and/or transdermally), inhalationally, buccally and/or orally, so as to treat a subject that benefits from administration of the therapeutic agent associated with, and/or dispersed within, the nanoparticle, and/or of the "free" therapeutic agent, which is not associated with, and/or dispersed within, the nanoparticle.

Liposomes usually comprise amphipathic phospholipid materials that form bilayer membranes that define and/or enclose the liposomes. They can have a single membrane (unilamellar), or multiple bilayers with a microscopic onion-like appearance. Liposomes can be rather large, measuring several microns in diameter. Liposomes generally have a spherical (or nearly spherical) shape, wherein the intact surface has no available "open" edges and thus cannot interact with other available "open" edge liposome(s) to undergo particle aggregation.

In contrast, phospholipid nanoparticles with diameters equal to or lower than about 200 nm have a restricted ability to bend into a spherical configuration, which should in principle be their thermodynamically stable structure. As a result, these low-diameter nanoparticles do not form a perfectly spherical particle, but rather a nearly planar sheet. Without wishing to be limited by any theory, those nearly planar sheets can be described as "nanodiscs" or "nanodisks" or "nanoFrisbees" or "bicelles." Such nanoparticles have "open" edges in their membranes, and these "edges" promote nanoparticle aggregation. As a result, in many instances the nanoparticles are generated as discrete particles, which than proceed to aggregate into larger, easily visible (wispy or feather-like) floating particles. This phenomenon may hamper the developability of the low-diameter nanoparticles as drug delivery agents. In certain embodiments, unlike in the case of liposomes, the API is not carried in the core volume of (or within) the bicelles. In other embodiments, the API is attached and/or bound to the membrane surface of the bicelles, either through a purely physical interaction or a covalent linkage. In one aspect, the present invention addresses this issue, providing compositions and methods that allow for closing the "open" edges of the nearly planar sheets (nanodiscs and/or nanoFrisbees) and thus minimizing or suppressing their tendency to self-aggregate.

As described herein, in certain embodiments, the lipid-based nanoparticles of the invention are useful as pharmaceutical carriers, and do not form the wispy, feathery-like structures described elsewhere herein. In certain embodiments, the nanoparticles of the invention comprise certain amphipathic lipids and/or certain organic molecules that enable the "open" edges of the planar nanoparticle membranes to be changed in a way that prevents aggregation of the nanoparticles.

In certain embodiments, appropriate closing of the "open" edges of the lipid-based nanoparticle is promoted by replacing a portion of distearoyl phosphatidylcholine [also known as (S)-2,3-bis(stearoyloxy)propyl (2-(trimethylammonio) ethyl) phosphate or DSPC, which comprises two $C_{18}$ acyl groups covalently linked to a glycerol backbone] with a $C_{12}$-$C_{24}$ acyl lysophosphatidylcholine [also known as $C_{12}$-$C_{24}$ acyl lysolecithin, or 1-($C_{12}$-$C_{24}$ acyl)-sn-glycero-3-phosphocholine, or (S)-2-hydroxy-3-($C_{12}$-$C_{24}$ acyloxy)propyl (2-(trimethylammonio)ethyl) phosphate, which comprises a single $C_{12}$-$C_{24}$ acyl group covalently linked to a glycerol backbone]:

4-methylphenol), prevents and/or minimizes the aggregation that occurs when that compound is omitted from the membrane. In other embodiments, the small molecule stabilizers or any salts and/or solvates thereof enable closure of any existing membrane "edges" in the nanoparticle.

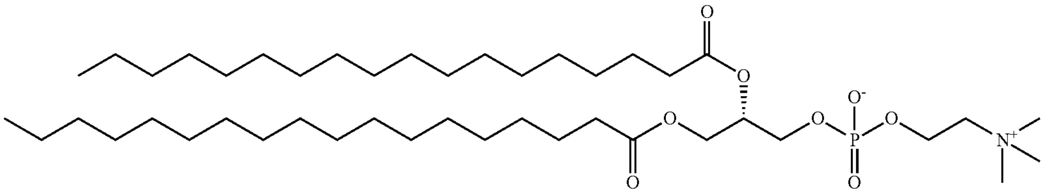

distearoyl phosphatidylcholine (DSPC)

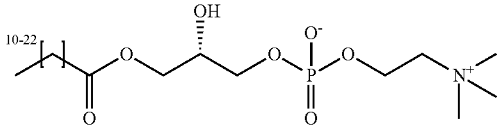

$C_{12}$-$C_{24}$ acyl lysophosphatidylcholine

In certain embodiments, appropriate closing of the "open" edges of the lipid-based nanoparticle is promoted by replacing a portion of distearoyl phosphatidylcholine [also known as (S)-2,3-bis(stearoyloxy)propyl (2-(trimethylammonio) ethyl) phosphate or DSPC, which comprises two $C_{18}$ acyl groups covalently linked to a glycerol backbone] with stearoyl lysophosphatidylcholine [also known as 1-steroyl-sn-glycero-3-phosphocholine, or (S)-2-hydroxy-3-(stearoyloxy)propyl (2-(trimethylammonio)ethyl) phosphate, which comprises a single $C_{18}$ acyl group covalently linked to a glycerol backbone]:

In certain embodiments, when incorporated into the membrane, any combinations of any of certain small molecule stabilizers or any salts and/or solvates thereof, and the $C_{12}$-$C_{24}$ acyl lysophosphatidylcholine, prevents and/or minimizes the aggregation that occurs when that compound is omitted from the membrane.

Compositions

The invention provides lipid-based nanoparticles, and compositions comprising the same. In certain embodiments, the nanoparticle comprises, and/or is defined by, a bipolar lipid membrane.

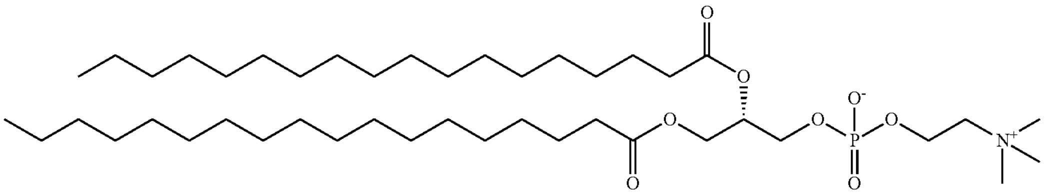

distearoyl phosphatidylcholine (DSPC)

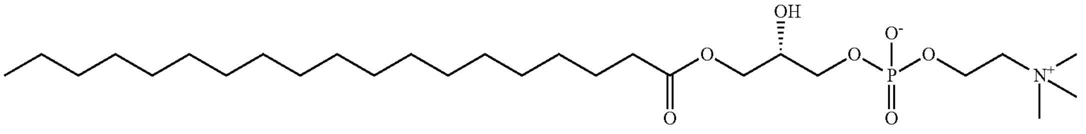

stearoyl lysophosphatidylcholine (SLPC)

In certain embodiments, when incorporated into the membrane, a $C_{12}$-$C_{24}$ acyl lysophosphatidylcholine (such as but not limited to stearoyl lysophosphatidylcholine) prevents and/or minimizes the aggregation that occurs when that compound is omitted from the membrane. In other embodiments, the $C_{12}$-$C_{24}$ acyl lysophosphatidylcholine (such as but not limited to stearoyl lysophosphatidylcholine), with its single aliphatic chain, enables closure of any existing membrane "edge" in the nanoparticle.

In certain embodiments, when incorporated into the membrane, any of certain small molecule stabilizers or any salts and/or solvates thereof, such as but not limited to m-cresol, benzyl alcohol, methyl 4-hydroxybenzoate, thiomersal, and butylated hydroxytoluene (also known as 2,6-di-tert-butyl- In certain embodiments, the membrane comprises cholesterol. In other embodiments, the membrane comprises dicetyl phosphate. In yet other embodiments, the membrane comprises an amphipathic lipid. In yet other embodiments, the membrane comprises 1,2-distearoyl-sn-glycero-3-phosphocholine (DSPC). In yet other embodiments, the membrane comprises cholesterol, dicetyl phosphate, and DSPC. In yet other embodiments, the membrane comprises a hepatocyte receptor binding molecule.

In certain embodiments, the amphipathic lipid comprises at least one selected from the group consisting of 1,2-distearoyl-sn-glycero-3-phosphocholine, 1,2-dipalmitoyl-sn-glycerol-[3-phospho-rac-(1-glycerol)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine. In other embodiments, the amphipathic lipid comprises at least one selected from the group consisting of 1,2-distearoyl-sn-glycero-3-phosphocholine, 1,2-dipalmitoyl-sn-glycero-3-phosphocholine, 1,2-dipalmitoyl-sn-glycero-3-[phospho-rac-(1-glycerol)], 1,2-distearoyl-sn-glycero-3-phosphoethanolamine, and 1,2-dipalmitoyl-sn-glycero-3-phosphoethanolamine-N-(succinyl).

In certain embodiments, the hepatocyte receptor binding molecule comprises biotin. In other embodiments, the biotin-containing hepatocyte receptor binding molecule comprises at least one selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE (2,3-diacetoxypropyl 2-(5-((3aS,6aR)-2-oxohexahydro-1H-thieno[3,4-d]imidazol-4-yl)pentanamido)ethyl phosphate); biotin-X-DHPE (2,3-diacetoxypropyl 2-(6-(5-((3aS,6aR)-2-oxohexahydro-1H-thieno[3,4-d]imidazol-4-yl)pentanamido)hexanamido) ethyl phosphate); 12-((biotinyl)amino) dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol) amine; (+) biotin 4-amidobenzoic acid sodium salt; Biotin 2-N-acetylamino-2-deoxy-f3-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; and biotin 6-O-phospho-α-D-mannopyranoside.

In certain embodiments, the hepatocyte receptor binding molecule is selected form the group consisting of 2,3-diacetoxypropyl 2-(5-((3aS,6aR)-2-oxohexahydro-1H-thieno[3,4-d]imidazol-4-yl)pentanamido)ethyl phosphate (biotin DHPE) and biotin-X-DHPE (2,3-diacetoxy propyl 2-(6-(5-((3aS,6aR)-2-oxohexahydro-1H-thieno[3,4-d]imidazol-4-yl)pentanamido) hexanamido)ethyl phosphate).

In certain embodiments, the cholesterol ranges from about 5% to about 25% (w/w) in the membrane. In other embodiments, the cholesterol is present in the membrane at a concentration of about 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% (w/w).

In certain embodiments, the dicetyl phosphate ranges from about 10% to about 25% (w/w) in the membrane. In other embodiments, the dicetyl phosphate is present in the membrane at a concentration of about 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% (w/w).

In certain embodiments, the DSPC ranges from about 40% to about 75% (w/w) in the membrane. In other embodiments, the DSPC is present in the membrane at a concentration of about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% (w/w).

In certain embodiments, the hepatocyte receptor binding molecule ranges from about 0.5% to about 10% (w/w) in the membrane. In other embodiments, the hepatocyte receptor binding molecule is present in the membrane at a concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5%, 5.5%, 6%, 6.5%, 7%, 7.5%, 8%, 8.5%, 9%, 9.5%, or 10% (w/w).

In certain embodiments, the membrane comprises at least one compound selected from the group consisting of a stabilizer and a $C_{12}$-$C_{24}$ acyl lysophosphatidylcholine.

In certain embodiments, the membrane further comprises a $C_{12}$-$C_{24}$ acyl lysophosphatidylcholine. In other embodiments, the membrane further comprises stearoyl lysophosphatidylcholine.

In certain embodiments, the membrane further comprises m-cresol.

In certain embodiments, the stabilizer is selected from the group consisting of m-cresol, benzyl alcohol, methyl 4-hydroxybenzoate, thiomersal, and butylated hydroxytoluene (2,6-di-tert-butyl-4-methylphenol).

In certain embodiments, the stabilizer ranges from about 10% to about 25% (w/w) in the membrane. In other embodiments, the stabilizer is present in the membrane at a concentration of about 10%, 11%, 12%, 13%, 14%, 15%, 16%, 17%, 18%, 19%, 20%, 21%, 22%, 23%, 24%, or 25% (w/w).

In certain embodiments, the m-cresol ranges from about 10% to about 25% (w/w) in the membrane. In other embodiments, the m-cresol is present in the membrane at a concentration of about 10%, 11%, 12%, 13%, 14%, 15%, 16%, 17%, 18%, 19%, 20%, 21%, 22%, 23%, 24%, or 25% (w/w).

In certain embodiments, the $C_{12}$-$C_{24}$ lysophosphatidylcholine ranges from about 5% to about 30% (w/w) in the membrane. In other embodiments, the $C_{12}$-$C_{24}$ lysophosphatidylcholine ranges from about 1% to about 30% (w/w) in the membrane. In yet other embodiments, the $C_{12}$-$C_{24}$ lysophosphatidylcholine is present in the membrane at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% (w/w).

In certain embodiments, the stearoyl lysophosphatidylcholine ranges from about 5% to about 30% (w/w) in the membrane. In other embodiments, the stearoyl lysophosphatidylcholine ranges from about 1% to about 30% (w/w) in the membrane. In yet other embodiments, the stearoyl lysophosphatidylcholine is present in the membrane at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% (w/w).

In certain embodiments, the amount of the $C_{12}$-$C_{24}$ lysophosphatidylcholine in the membrane is about 1% to about 30% (w/w) of the amount of DSPC in the membrane. In yet other embodiments, the amount of the $C_{12}$-$C_{24}$ lysophosphatidylcholine in the membrane is about 1%, 2%, 3%, 4%, 5%, 6%, 7%, 8%, 9%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% (w/w) or 30% (w/w) of the amount of DSPC in the membrane.

In certain embodiments, the amount of the $C_{12}$-$C_{24}$ lysophosphatidylcholine in the membrane is about 1 mole % to about 50 mole % of the amount of DSPC in the membrane. In yet other embodiments, the amount of the $C_{12}$-$C_{24}$ lysophosphatidylcholine in the membrane is about 1, 2, 3, 4, 5, 6, 7, 8, 9, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mole % of the amount of DSPC in the membrane.

In certain embodiments, the amount of the stearoyl lysophosphatidylcholine in the membrane is about 1% to about 30% (w/w) of the amount of DSPC in the membrane. In yet other embodiments, the amount of the stearoyl lysophosphatidylcholine in the membrane is about 1%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% (w/w) of the amount of DSPC in the membrane.

In certain embodiments, the amount of the stearoyl lysophosphatidylcholine in the membrane is about 1 mole % to about 50 mole % of the amount of DSPC in the membrane. In yet other embodiments, the amount of the stearoyl lysophosphatidylcholine in the membrane is about 1, 2, 3, 4, 5, 6, 7, 8, 9, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mole % of the amount of DSPC in the membrane.

In certain embodiments, the membrane comprises cholesterol, dicetyl phosphate, DSPC, stearoyl lysophosphatidylcholine, m-cresol, and at least one selected from the group consisting of biotin DHPE and biotin-X-DHPE. In other embodiments, the membrane comprises cholesterol, dicetyl phosphate, DSPC, stearoyl lysophosphatidylcholine, m-cresol, and biotin DHPE.

In certain embodiments, the membrane comprises cholesterol, dicetyl phosphate, DSPC, m-cresol, and at least one selected from the group consisting of biotin DHPE and biotin-X-DHPE. In other embodiments, the membrane comprises cholesterol, dicetyl phosphate, DSPC, m-cresol, and biotin DHPE.

In certain embodiments, the membrane comprises cholesterol, dicetyl phosphate, DSPC, stearoyl lysophosphatidylcholine, and at least one selected from the group consisting of biotin DHPE and biotin-X-DHPE. In other embodiments, the membrane comprises cholesterol, dicetyl phosphate, DSPC, stearoyl lysophosphatidylcholine, and biotin DHPE.

In certain embodiments, the stabilizer is contacted with the membrane, and/or the lipid components that assemble to form the membrane (such as, but not limited to, cholesterol, dicetyl phosphate, DSPC, $C_{12}$-$C_{24}$ lysophosphatidylcholine if present, and biotin DHPE), at a (w/w) ratio of the membrane to the stabilizer ranging from about 1:1 to about 1:30. In other embodiments, the stabilizer is contacted with the membrane, and/or the lipid components that assemble to form the membrane, at a (w/w) ratio of the membrane to the stabilizer of about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, 1:20, 1:21, 1;22, 1:23, 1:24, 1:25, 1:26, 1:27, 1:28, 1:29 or 1:30.

In certain embodiments, the m-cresol is contacted with the membrane, and/or the lipid components that assemble to form the membrane (such as, but not limited to, cholesterol, dicetyl phosphate, DSPC, $C_{12}$-$C_{24}$ lysophosphatidylcholine if present, and biotin DHPE), at a (w/w) ratio of the membrane to the stabilizer ranging from about 1:1 to about 1:30. In other embodiments, the m-cresol is contacted with the membrane, and/or the lipid components that assemble to form the membrane, at a (w/w) ratio of the membrane to the stabilizer of about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, 1:20, 1:21, 1;22, 1:23, 1:24, 1:25, 1:26, 1:27, 1:28, 1:29 or 1:30.

In certain embodiments, the membrane comprises cholesterol, dicetyl phosphate, DSPC, stearoyl lysophosphatidylcholine, m-cresol, and biotin DHPE, in a % (w/w) ratio of about 9.4:18.1:56.8:14.1:0.0:1.5.

In certain embodiments, the membrane comprises cholesterol, dicetyl phosphate, DSPC, stearoyl lysophosphatidylcholine, and biotin DHPE, in a % (w/w) ratio of about 9.4:18.1:56.8:14.1:1.5.

In certain embodiments, the membrane comprises cholesterol, dicetyl phosphate, DSPC, stearoyl lysophosphatidylcholine, m-cresol, and biotin DHPE, in a % (w/w) ratio of about 7.7:15.0:58.6:0.0:17.4:1.3.

In certain embodiments, the membrane comprises cholesterol, dicetyl phosphate, DSPC, and biotin DHPE, in a % (w/w) ratio of about 9.3:18.2:71.0:1.5.

In certain embodiments, the membrane comprises cholesterol, dicetyl phosphate, DSPC, stearoyl lysophosphatidylcholine, m-cresol, and biotin DHPE, in a % (w/w) ratio of about 8.4:16.2:47.5:7.6:19.0:1.3.

In certain embodiments, the membrane comprises cholesterol, dicetyl phosphate, DSPC, stearoyl lysophosphatidylcholine, and biotin DHPE, in a % (w/w) ratio of about 10.4:20:58.6:9.4:1.6.

In certain embodiments, the at least one hepatocyte receptor binding molecule extends outward from the nanoparticle.

The invention should not be construed to be limited to the constructs described and/or exemplified herein. Rather, the invention provides methods of stabilizing and/or preventing aggregation of liposomes and other lipid-based nanoparticles, wherein the membrane is contacted with at least one selected from the group consisting of a stabilizer and a $C_{12}$-$C_{24}$ acyl lysophosphatidylcholine. In certain embodiments, the contacting removes or minimizes any "free" edges in the membrane that lead to aggregation of the liposomes and other lipid-based nanoparticles.

In certain embodiments, the stabilizer is selected from the group consisting of m-cresol, benzyl alcohol, methyl 4-hydroxybenzoate, thiomersal, and butylated hydroxytoluene. In other embodiments, the stabilizer, such as but not limited to m-cresol, ranges from about 10% to about 25% (w/w) in the membrane. In yet other embodiments, the stabilizer, such as but not limited to m-cresol, is present in the membrane at a concentration of about 10%, 11%, 12%, 13%, 14%, 15%, 16%, 17%, 18%, 19%, 20%, 21%, 22%, 23%, 24%, or 25% (w/w).

In certain embodiments, the $C_{12}$-$C_{24}$ lysophosphatidylcholine, such as but not limited to stearoyl lysophosphatidylcholine, ranges from about 5% to about 30% (w/w) in the membrane. In other embodiments, the $C_{12}$-$C_{24}$ lysophosphatidylcholine, such as but not limited to stearoyl lysophosphatidylcholine, ranges from about 1% to about 30% (w/w) in the membrane. In yet other embodiments, the $C_{12}$-$C_{24}$ lysophosphatidylcholine, such as but not limited to stearoyl lysophosphatidylcholine, is present in the membrane at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% (w/w).

In certain embodiments, the membrane comprises at least one amphipathic lipid selected from the group consisting of 1,2-distearoyl-sn-glycero-3-phosphocholine, 1,2-dipalmitoyl-sn-glycerol-[3-phospho-rac-(1-glycerol)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine. In other embodiments, the amphipathic lipid is at least one selected from the group consisting of 1,2-distearoyl-sn-glycero-3-phosphocholine, 1,2-dipalmitoyl-sn-glycero-3-phosphocholine, 1,2-dipalmitoyl-sn-glycero-3-[phospho-rac-(1-glycerol)], 1,2-distearoyl-sn-glycero-3-phosphoethanolamine, and 1,2-dipalmitoyl-sn-glycero-3-phosphoethanolamine-N-(succinyl).

In certain embodiments, the amount of the $C_{12}$-$C_{24}$ lysophosphatidylcholine in the membrane is about 1%-30% (w/w) of the amount of the at least one amphipathic lipid in the membrane. In yet other embodiments, the amount of the $C_{12}$-$C_{24}$ lysophosphatidylcholine in the membrane is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% (w/w) of the amount of the at least one amphipathic lipid in the membrane.

In certain embodiments, the amount of the $C_{12}$-$C_{24}$ lysophosphatidylcholine in the membrane is about 1 mole % to about 50 mole % of the amount of the at least one amphipathic lipid in the membrane. In yet other embodiments, the amount of the $C_{12}$-$C_{24}$ lysophosphatidylcholine in the membrane is about 1, 2, 3, 4, 5, 6, 7, 8, 9, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mole % of the amount of the at least one amphipathic lipid in the membrane.

In certain embodiments, the stabilizer, such as but not limited to m-cresol, is contacted with the membrane, and/or the lipid components that assemble to form the membrane, at a (w/w) ratio ranging from about 1:1 to about 1:30. In other embodiments, the stabilizer, such as but not limited to m-cresol, is contacted with the membrane, and/or the lipid components that assemble to form the membrane, at a (w/w) ratio of about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:16, 1:17, 1:18, 1:19, 1:20, 1:21, 1;22, 1:23, 1:24, 1:25, 1:26, 1:27, 1:28, 1:29 or 1:30.

In certain embodiments, the size of the nanoparticle ranges from about 10 nm to about 150 nm. In other embodiments, the size of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm or 150 nm.

In certain embodiments, a therapeutic agent (such as, but not limited to, insulin) is dispersed within and/or adsorbed onto the nanoparticle. In other embodiments, the therapeutic agent is covalently bound to the nanoparticle. In yet other embodiments, the therapeutic agent is not covalently bound to the nanoparticle.

In certain embodiments, the therapeutic agent comprises at least one selected from the group consisting of insulin, insulin analogs, amylin, interferon, parathyroid hormone, calcitonin, serotonin, serotonin agonist, serotonin reuptake inhibitor, human growth hormone, GIP, anti-GIP monoclonal antibody, metformin, bromocriptine, dopamine, glucagon and GLP-1. In other embodiments, the therapeutic agent is insulin.

In certain embodiments, the nanoparticle is suspended in an aqueous solution comprising a free dissolved therapeutic agent that is not dispersed within the nanoparticle.

In certain embodiments, the nanoparticle-dispersed insulin and the free dissolved insulin are independently selected from the group consisting of insulin lispro, insulin aspart, regular insulin, insulin glargine, insulin zinc, extended human insulin zinc suspension, isophane insulin, human buffered regular insulin, insulin glulisine, recombinant human regular insulin, and recombinant human insulin isophane.

In certain embodiments, the lipid further comprises cellulose acetate phthalate. In other embodiments, the cellulose acetate phthalate is at least partially bound to the therapeutic agent dispersed within the nanoparticle.

In certain embodiments, at least one charged organic molecule is bound to the therapeutic agent dispersed within the nanoparticle. In other embodiments, the charged organic molecule is at least one selected from the group consisting of protamines, polylysine, poly(arg-pro-thr)n in a mole ratio of 1:1:1, poly(DL-Ala-poly-L-lys)n in a mole ratio of 6:1, histones, sugar polymers comprising a primary amino group, polynucleotides with primary amino groups, proteins comprising amino acid residues with carboxyl ($COO^-$) or sulfhydral ($S^-$) functional groups, and acidic polymers (such as sugar polymers containing carboxyl groups).

In certain embodiments, the nanoparticle of the invention, and compositions comprising the same, help deliver the therapeutic agent dispersed therewithin to the hepatocytes in the liver.

In certain embodiments, the compositions of the invention comprise an effective dose of a hepatocyte targeted pharmaceutical composition that combines free therapeutic drug (such as, but not limited to, insulin) and therapeutic drug associated with the lipid-based nanoparticle of the invention. The combination of free therapeutic drug and therapeutic drug associated with the lipid-based nanoparticle creates a dynamic equilibrium process between the two forms of therapeutic drug that occurs in vivo to help control the movement of free therapeutic drug to the receptor sites of hormonal action. In the case of insulin as the therapeutic drug, those receptor sites are the muscle and adipose tissues of a diabetic patient. Hepatocyte targeted therapeutic drug is also delivered to the liver of a patient over a different designated time period than free therapeutic drug, thereby introducing new pharmacodynamic profiles of therapeutic drug when the therapeutic drug remains associated with the nanoparticle and/or when free therapeutic drug is released from the nanoparticle. In addition, a portion of therapeutic drug that is associated with the nanoparticle is targeted to the liver. In the case of insulin as the therapeutic drug, the new pharmacodynamic profile of the product provides not only basal insulin for peripheral tissues, but also meal-time hepatic therapeutic drug stimulation for the management of hepatic glucose storage during a meal. Free insulin is released from the site of administration and is distributed throughout the body. Insulin associated with the lipid-based nanoparticle is delivered to the liver. The rate of release of insulin associated with the nanoparticle is different than the rate of release of free insulin from the site of administration. These different release rates of insulin delivery, combined with the targeted delivery of insulin associated with the nanoparticle to the liver, provide for the normalization of glucose concentrations in patients with Type 1 and Type 2 diabetes mellitus. In certain embodiments, the hepatocyte targeted composition comprises any therapeutically effective insulin or insulin derivative or analog, or any combination of two or more types of insulin or insulin derivative or analog.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and 35 S. In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Compounds of the invention can in certain embodiments form acids or bases. In certain embodiments, the invention contemplates acid addition salts. In other embodiments, the invention contemplates base addition salts. In yet other embodiments, the invention contemplates pharmaceutically acceptable acid addition salts. In yet other embodiments, the invention contemplates pharmaceutically acceptable base addition salts. Pharmaceutically acceptable salts refer to salts of those bases or acids that are not toxic or otherwise biologically undesirable.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium, lithium and copper, iron and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Disclosed is a kit comprising any composition of the invention and an instructional material which describes administering the composition to a tissue of a subject, such as a mammal. This kit may comprise a (preferably sterile) solvent suitable for dissolving or suspending the composition of the invention prior to administering the composition to the subject, such as a mammal.

Methods

The invention provides methods of preparing the lipid-based nanoparticle of the invention. In certain embodiments, the method comprises contacting in an aqueous system cholesterol, dicetyl phosphate, amphipathic lipid, and hepatocyte receptor binding molecule. In other embodiments, the method comprises contacting in an aqueous system cholesterol, dicetyl phosphate, amphipathic lipid, hepatocyte receptor binding molecule, and at least one compound selected from the group consisting of a stabilizer and stearoyl lysophosphatidylcholine. In yet other embodiments, the method comprises contacting in an aqueous system cholesterol, dicetyl phosphate, DSPC, and biotin-DHPE. In yet other embodiments, the method comprises contacting in an aqueous system cholesterol, dicetyl phosphate, DSPC, stearoyl lysophosphatidylcholine, m-cresol, and biotin-DHPE.

In certain embodiments, the nanoparticle is formed in the absence of the therapeutic agent, wherein optionally the nanoparticle is at least partially concentrated, purified or isolated, and wherein the therapeutic agent is contacted with the nanoparticle, whereby at least a portion of the therapeutic agent is dispersed within the nanoparticle.

In certain embodiments, the composition is treated with cellulose acetate phthalate, which can bind non-covalently to at least a portion of the therapeutic agent dispersed within the nanoparticle and protect the therapeutic agent from metabolic degradation. In other embodiments, the cellulose acetate phthalate is covalently bound to the therapeutic agent and/or any of the lipids that constitute the nanoparticle.

Further embodiments relating to certain methods for preparing and/or processing and/or purifying a nanoparticle can be found, for example, in U.S. Patent Application Nos. US20110135725 and US20090087479 and PCT Patent Application Publication No. WO 2018/169954, all of which are incorporated herein in their entireties by reference.

The invention further provides a method of treating a disease in a mammal. In certain embodiments, the method comprises administering to the mammal in need thereof a therapeutically effective amount of a nanoparticle and/or a composition of the invention.

In certain embodiments, the disease is diabetes mellitus and the therapeutic agent comprises insulin.

Administration/Dosage/Formulations

The invention also encompasses pharmaceutical compositions and methods of their use. These pharmaceutical compositions may comprise an active ingredient (which can be one or more compositions of the invention, or pharmaceutically acceptable salts thereof) optionally in combination with one or more pharmaceutically acceptable agents. The compositions set forth herein can be used alone or in combination with additional compounds to produce additive, complementary, or synergistic effects.

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection, or may be administered inhalationally, buccally and/or orally. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect, and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated herein.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils, as long as the solvent or dispersion medium does not disrupt the nanoparticle significantly. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In certain embodiments, the dose of a compound and/or composition of the invention is from about 1 mg and about 2,500 mg. In other embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in other embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound and/or composition of the invention, alone or in combination with a second pharmaceutical agent; and instructions for using the compound to treat, prevent, or reduce one or more symptoms of a disease or disorder contemplated herein.

In certain embodiments, the container holds a lipid-based nanoparticle, which does not comprise a therapeutic agent of interest, such as but not limited to an insulin or a derivative or analog thereof. In other embodiments, the container holds a lipid-based nanoparticle, which comprises a therapeutic agent of interest, such as but not limited to an insulin or a derivative or analog thereof. In yet other embodiments, the container further holds a therapeutic agent of interest, such as but not limited to an insulin or a derivative or analog thereof.

Illustrative Non-Limiting Methods of Treating Diabetes Mellitus

Patients with Type 1 or Type 2 diabetes mellitus can be administered an effective amount of a nanoparticle of the invention comprising an insulin. When this composition is administered subcutaneously, a portion of the composition enters the circulatory system where the composition is transported to the liver and other areas. The extended amphipathic lipid binds the lipid construct to receptors of hepatocytes. A portion of the administered composition is exposed to an external gradient in vivo, where insulin can be solubilized and then move from the lipid construct thereby supplying insulin to the muscle and adipose tissue. Insulin that remains with the lipid construct maintains the capability of being directed to the hepatocyte binding receptor on the hepatocytes in the liver. Therefore, two forms of insulin are produced from this particular lipid construct. In an in vivo setting, free and lipid associated insulin are generated in a time-dependent manner.

Administration of the nanoparticles and compositions comprising same can be through any of the accepted modes of administration for insulin that are desired to be administered. These methods include oral, parenteral, nasal and other systemic or aerosol forms. These methods further include pump delivery systems.

Oral administration of a nanoparticle of the invention is followed by intestinal absorption of insulin associated with the nanoparticle of the invention into the circulatory system of the body, where it is also exposed to the physiological pH of the blood. The nanoparticle is targeted for delivery to the liver and may be shielded by the presence of cellulose acetate phthalate within the nanoparticle of the invention. In the case of oral administration, the shielded nanoparticle transverses the oral cavity, migrates through the stomach and moves into the small intestine, where the alkaline pH of the small intestine degrades the cellulose acetate phthalate shield. The deshielded nanoparticle is absorbed into the circulatory system. This enables the nanoparticle to be delivered to the sinusoids of the liver. A receptor binding molecule, such as 1,2-dipalmitoyl-sn-glycero-3-phosphoethanolamine-N-(Cap Biotinyl) or any other hepatocyte specific molecule, provides a means for lipid construct to bind to the receptor and then be engulfed or endocytosed by the hepatocytes. Insulin is then released from the nanoparticle where, upon gaining access to the cellular environment, it performs its designated function with regard to acting as an agent to control diabetes mellitus.

Patients with Type 1 or Type 2 diabetes mellitus may be administered an effective amount of a nanoparticle comprising a mixture of free glargine insulin and glargine insulin associated with the nanoparticle. Glargine insulin can be combined with other forms of insulin, such as insulin lispro, insulin aspart, regular insulin, insulin zinc, human insulin zinc extended, isophane insulin, human buffered regular insulin, insulin glulisine, recombinant human regular insulin, recombinant human insulin isophane or premixed combinations of any of the aforementioned insulins, a derivative thereof, and a combination of any of the aforementioned insulins. The composition can be administered by a subcutaneous or oral route.

After a composition is administered to a patient by subcutaneous injection, the in situ physiological environment in the injection area, the morphology and chemical structures of free insulin and the insulin associated with the nanoparticle begin to change. For example, as the pH of the environment around the free glargine insulin and the glargine insulin associated with the nanoparticle increases after being diluted with physiological media, the pH reaches the isoelectric point of glargine insulin, where flocculation, aggregation and precipitation reactions occur for both free glargine insulin and glargine insulin associated with the nanoparticle. In certain embodiments, free glargine insulin changes from a soluble form at injection, to a insoluble form at a pH near its isoelectric point of pH 5.8-6.2, and then to a soluble form at physiological pH. The rates at which these processes occur differ between free glargine insulin and glargine insulin associated with the nanoparticle. The free glargine insulin is directly exposed to changes in pH and dilution. Exposure of glargine insulin associated with the nanoparticle to small changes in pH and dilution at physiological pH is delayed due to the time required for diffusion of physiological fluids or media through the lipid bilayer in the nanoparticle. The delay in the release of insulin from the lipid construct as well as the delay of the release of the insulin associated with the nanoparticle is a feature of the invention since it affects and augments the biological and pharmacological response in vivo.

Oral administration of a pharmaceutical composition that combines free glargine insulin and glargine insulin associated with a nanoparticle is followed by intestinal absorption of glargine insulin associated with the nanoparticle into the circulatory system of the body, where it is also exposed to the physiological pH of the blood. In certain embodiments, the composition comprises a delayed release matrix which releases HDV glargine over a prolonged period of time, in order to achieve a 24-hour dose regimen. All or a portion of the nanoparticle is delivered to the liver.

Patients with Type 1 or Type 2 diabetes mellitus can be administered an effective amount of a hepatocyte targeted composition comprising a mixture of free recombinant human insulin isophane (NPH) plus free recombinant human regular insulin along with recombinant human insulin isophane and recombinant human regular insulin which are both associated with a nanoparticle. Recombinant human insulin isophane can be combined with other forms of insulin, such as insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, or any (premixed) combinations thereof.

In certain embodiments, the composition comprises a delayed release matrix which releases HDV NPH over a prolonged period of time, in order to achieve a 24-hour dose regimen.

Oral administration of a pharmaceutical composition that combines free recombinant human insulin isophane and recombinant human insulin isophane associated with a nanoparticle is followed by intestinal absorption of recombinant human insulin isophane associated with the nanoparticle into the circulatory system of the body where it is also exposed to the physiological pH of the blood. All or a portion of the nanoparticle is delivered to the liver, while the non-HDV isophane is slowly absorbed from a slow release matrix for release into the general circulation.

As the physiological dilution is increased in situ in the subcutaneous space or upon entering into the circulatory system, free recombinant human insulin isophane and recombinant human insulin isophane associated with the nanoparticle encounter a normal physiological pH environment of pH 7.4. As a result of dilution free recombinant human insulin isophane changes from an insoluble form at injection, to a soluble form at physiological pH. In the soluble form, recombinant human insulin isophane migrates through the body to sites where it is capable of eliciting a pharmacological response. Recombinant human insulin isophane associated with the nanoparticle becomes solubilized and released from the nanoparticle at a different rate that is slower than that of free recombinant human insulin isophane. This is because recombinant human insulin isophane associated with the nanoparticle has to traverse the core volume and lipid domains of the nanoparticle before it contacts the bulk phase media.

The amount of insulin administered will be dependent on the subject being treated, the type and severity of the affliction, the manner of administration and the judgment of the prescribing physician. Although effective dosage ranges for specific biologically active substances of interest are dependent upon a variety of factors and are generally known to one of ordinary skill in the art, some dosage guidelines can be generally defined. For most forms of administration, the nanoparticle will be suspended in an aqueous solution and generally not exceed 4.0% (w/v) of the total formulation. The drug component of the formulation will in certain embodiments be less than 20% (w/v) of the formulation and generally greater than 0.01% (w/v).

In certain embodiments, the pharmaceutical composition comprises HDV insulin, and no free insulin. In such cases, all of the insulin within the composition is targeted to the liver. In other embodiments, the pharmaceutical composition comprises HDV insulin and free insulin (non-HDV insulin). The ratio between HDV insulin and free insulin can be, in non-limiting example, about 0.1:99.9, 0.2:99.8, 0.3:99.7, 0.4:99.6, 0.5:99.5, 0.6:99.4, 0.7:99.3, 0.8:99.2, 0.9:99.1, 1:99, 2:98, 3:97, 4:96, 5:95, 6:94, 7:93, 8:92, 9:91, 10:90, 12:88, 14:86, 16:84, 18:82, 20:80, 22:78, 24:76, 25:75, 26:74, 28:72, 30:70, 32:68, 34:66, 36:64, 38:62, 40:60, 42:58, 44:56, 46:54, 48:52, and/or 50:50.

Dosage forms or compositions containing active ingredient in the range of 0.005% to 5% with the balance made up from non-toxic carriers can be prepared.

The exact composition of these formulations may vary widely depending on the particular properties of the drug in question. In certain embodiments, they comprise from 0.01% to 5%, and preferably from 0.05% to 1% active ingredient for highly potent drugs, and from 2%-4% for moderately active drugs.

The percentage of active ingredient contained in such parenteral compositions is highly dependent on the specific nature thereof, as well as the activity of the active ingredient and the needs of the subject. However, percentages of active ingredient of 0.01% to 5% in solution are employable, and will be higher if the composition is a solid which will be subsequently diluted to the above percentages. In certain embodiments, the composition comprises 0.2%-2.0% of the active agent in solution.

Administration

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds and/or compositions for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds and/or compositions of the invention may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds and/or compositions of the invention, and a further layer providing for the immediate release of a medication for treatment of diseases or disorders. Using a wax/pH-sensitive polymer mix, a gastric insoluble composition may be obtained in which the active ingredient is entrapped, ensuring its delayed release.

Parenteral Administration

For parenteral administration, the compounds and/or compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Pulmonary Administration

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 microns, and preferably from about 1 to about 6 microns. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 microns and at least 95% of the particles by number have a diameter less than 7 microns. More preferably, at least 95% of the particles by weight have a diameter greater than 1 nanometer and at least 90% of the particles by number have a diameter less than 6 microns. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile for administration by injection, comprising the active ingredient, and may conveniently be administered using any nebulization or atomization device. In certain embodiments, the compounds and/or compositions of the invention are sterile filtered before administration to the subject. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 microns.

Intranasal Delivery

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 microns. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 75% (w/w) of the active ingredient, and may further comprise one or more of the additional ingredients described herein.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compositions may be formulated with a suitable polymer or hydrophobic material that provides sustained release properties to the compounds and/or compositions. As such, the compositions and/or compositions for use the method of the invention may be administered in the form of microparticles, for example, by injection or in the form of wafers or discs by implantation.

In certain embodiments, the compounds and/or compositions of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound and/or composition of the present invention depends on the age, sex and weight of the patient, the current medical condition of the patient and the progression of a disease or disorder contemplated herein in the patient being treated. The skilled artisan is able to determine appropriate dosages depending on these and other factors.

A suitable dose of a compound and/or composition of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound and/or composition dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds and/or compositions for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the LD 50 (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds and/or compositions lies preferably within a range of circulating concentrations that include the $ED_{50}$ with minimal toxicity. The dosage optionally varies within this range depending upon the dosage form employed and the route of administration utilized.

Definitions

Unless defined otherwise, all technical and scientific terms used herein generally have the same meaning as commonly understood by one of ordinary skill in the art to which the invention belongs. Generally, the nomenclature used herein and the laboratory procedures in organic chemistry and protein chemistry are those well known and commonly employed in the art.

The articles "a" and "an" are used herein to refer to one or to more than one (i.e., to at least one) of the grammatical object of the article. By way of example, "an element" means one element or more than one element.

The term "A1c" or "A1C" or "HbA1C" or "hemoglobin A1c" or "HBA1C" or "HgbA1c" or "haemoglobin A1c" or "HbA1c" or "Hb1c" refers to a form of hemoglobin that is covalently bound to glucose. A1c is formed in a non-enzymatic glycation pathway by hemoglobin's exposure to plasma glucose. A1c is measured primarily to identify the three-month average plasma glucose concentration, and thus can be used as a diagnostic test for diabetes and as assessment test for glycemic control in people with diabetes. The ratio of A1c to total hemoglobin (% A1c) (generally measured as mass/mass) is used to diagnose diabetes (according to 1993 Diabetes Control and Complications Trial or DCCT): normal individuals have less than 5.7% A1, pre-diabetic individuals have 5-7-6.4% A1c, and diabetic individuals have greater than 6.5% A1c. The DCCT % A1c value can be converted to the International Federation of Clinical Chemistry and Laboratory Medicine (IFCC) units using the formula:

$$\text{IFCC HbA1c(mmol/mol)}=[\text{DCCT HbA1c(\%)}-2.14]\times 10.929$$

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "active ingredient" refers to a therapeutic agent that is to be delivered to a subject to produce a therapeutic effect in the subject. Non-limiting examples of active ingredients contemplated within the invention are insulin, interferon, parathyroid hormone, calcitonin, serotonin, serotonin agonist, serotonin reuptake inhibitor, human growth hormone, GIP, anti-GIP monoclonal antibody, metformin, bromocriptine, dopamine, glucagon and/or GLP-1.

The term "amphipathic lipid" means a lipid molecule having a polar and non-polar end.

By "aqueous media" is meant water or water containing buffer or salt.

As used herein, the term "basal insulin" or "background insulin" is insulin that is taken to keep blood glucose levels at consistent levels during periods of fasting. Basal insulin is thus needed to keep blood glucose levels under control, and to allow the cells to take in glucose for energy. Basal insulin is usually taken once or twice a day depending on the insulin. Basal insulin needs to act over a relatively long period of time, and thus is either long acting insulin or intermediate insulin.

As used herein, the term "basal glucose control" refers to the glucose control that is afforded by use of basal insulin, or an equivalent thereof.

The term "bioavailability" refers to a measurement of the rate and extent that insulin reaches the systemic circulation and is available at the sites of action.

As used herein, the term "bolus insulin" refers to insulin that is specifically taken just before, at, or just after meal times to keep blood glucose levels under control following a meal. Bolus insulin needs to act quickly and is generally short acting insulin or rapid acting insulin.

As used herein, the term "bolus glucose control" refers to the glucose control that is afforded by use of bolus insulin, or an equivalent thereof.

In one aspect, the terms "co-administered" and "co-administration" as relating to a subject refer to administering to the subject a compound of the invention or salt thereof along with a compound that may also treat any disease or disorder contemplated herein and/or with a compound that is useful in treating other medical conditions but which in themselves may cause or facilitate any disease or disorder contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "ED 50" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

The term "free active ingredient" or "free therapeutic agent" refers to an active ingredient or therapeutic agent that is not dispersed within the lipid particle (i.e., located within, adsorbed on and/or bound to the lipid particle membrane).

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is $20^{A}$-Gly- $30^B$a-L-Arg-$30^B$b-L-Arg-human insulin and has the empirical formula $C_{267}H_{404}N_{72}O_{78}S_6$ and a molecular weight of 6063.

As used herein, the term "hyperinsulinemia" refers to a condition in which there are excess levels of insulin circulating in the blood relative to the level of glucose. Hyperinsulinemia can be an unwanted side effect of administration of exogenous insulin to a diabetic patient (thus being a form of iatrogenic hyperinsulinemia; see Cryer, 2008, Diabetes 57(12):3169-76, McCrinson & Sherwin, 2010, Diabetes 59(10):2333-9; Wang, et al., 2013, J. Diab. & Its Compl. 27(1):70-74; all of which are incorporated herein in their entireties by reference). That condition can trigger complications such as metabolic disease, hypoglycemia, increased risk of polycystic ovary syndrome (PCOS), increased synthesis of VLDL (hypertriglyceridemia), hypertension (insulin increases sodium retention by the renal tubules), coronary artery disease (CAD; increased insulin damages endothelial cells), increased risk of cardiovascular disease, and/or weight gain and lethargy.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The term "insulin" refers to natural or recombinant forms of insulin, and derivatives of the aforementioned insulins. Examples of insulin include, but are not limited to insulin lispro (such as, for example, ADMELOG®, Sanofi), insulin aspart (such as, for example, FIASP®, Novo Nordisk), regular insulin, insulin glargine (such as, for example, BASAGLAR®, Lilly), insulin zinc, human insulin zinc extended, isophane insulin, human buffered regular insulin, insulin glulisine, recombinant human regular insulin, and recombinant human insulin isophane. Also included are animal insulins, such as bovine or porcine insulin.

As used herein, the term "iotrogenic" refers to any illness caused by a medical examination or treatment.

The term "isoelectric point" refers to the pH at which the concentrations of positive and negative charges on the protein are equal and, as a result, the protein will express a net zero charge. At the isoelectric point, a protein will exist almost entirely in the form of a zwitterion, or hybrid between forms of the protein. Proteins are least stable at their isoelectric points, and are more easily coagulated or precipitated at this pH. However, proteins are not denatured upon isoelectric precipitation since this process is essentially reversible.

The term "lipid construct" refers to a lipid and/or phospholipid particle in which individual lipid molecules interact to create a bipolar lipid membrane that defines the boundaries of the lipid construct.

As the term is used herein, "to modulate" or "modulation of" a biological or chemical process or state refers to the alteration of the normal course of the biological or chemical process, or changing the state of the biological or chemical process to a new state that is different than the present state. For example, modulation of the isoelectric point of a polypeptide may involve a change that increases the isoelectric point of the polypeptide. Alternatively, modulation of the isoelectric point of a polypeptide may involve a change that decreases the isoelectric point of a polypeptide.

The term "non-glargine insulin" refers at all insulins, either natural or recombinant that are not glargine insulin. The term includes insulin-like moieties, including fragments of insulin molecules, that have biological activity of insulins.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. In certain embodiments, the subject is human.

The term "treat," "treating" or "treatment," as used herein, means reducing the frequency or severity with which symptoms of a disease or condition are experienced by a subject by virtue of administering an agent or compound to the subject.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, point out specific embodiments of the present invention, and are not to be construed as limiting in any way the remainder of the disclosure.

The materials and methods used in the experiments presented in this Experimental Example are now described.

Example 1: Divergent Hypoglycemic Effects of Hepatic Directed Prandial Insulin—A Six-Month Study in Type 1 Diabetes Mellitus (T1DM)

In one aspect, HDV-I is an insulin-agnostic delivery system that utilizes a biotin-containing lipid (such as but not limited to biotin-phosphatidylethanolamine) in a phospholipid matrix, targeting insulin to the liver. Mimicking portal vein delivery, subcutaneous (SC) injection of HDV-I provides a more physiologic treatment paradigm. Treatment with SC HDV-human regular insulin (RHI) reduces post-prandial glucose excursions compared to SC RHI. Without wishing to be limited by any theory, HDV-I's flat dose-response effect on hepatic glucose balance in preclinical studies supports a fixed combination for treatment.

In the present study the use of HDV-insulin lispro (HDV-L) vs. insulin lispro (LIS) in treating type 1 diabetes mellitus (T1DM) was assessed. HDV-L in this study contained 1% HDV-bound LIS and 99% unbound LIS.

ISLE-1 was a 26-week, Phase 2b, multicenter, randomized, double-blind, non-inferiority trial. Among 176 randomized patients (HDV-L, n=118; LIS, n=58), difference in change from baseline A1c at Week 26 was +0.09% (95% CI −0.18% to 0.35%), confirming non-inferiority (pre-specified margin 0.4%). Baseline A1c modified the treatment group effect on hypoglycemia risk (interaction p-value $<0.001$), with less risk of hypoglycemia (and lower insulin dosing with similar A1c outcome) with HDV-L compared to LIS at higher A1c, but opposite hypoglycemia effects at lower A1c (despite similar A1c and insulin dosing). No safety signals were identified. The present results indicate that HDV-L's hepatic biodistribution appears to potentiate insulin effect in T1DM.

a. Design and Methods

Design and Participants

ISLE-1 was a 26-week, Phase 2b, multicenter, randomized, double-blind, trial in T1DM treated with multiple daily injections (MDI) of insulin. The primary objective was A1c non-inferiority with 26 weeks of HDV-L versus LIS.

Main inclusion criteria were: age ≥18 years; T1D for ≥12 months; A1c ≥7.0 (≥58 mmol/mol) to ≤10.5% (≤91 mmol/mol); treated with insulins glargine or detemir for basal coverage. Main exclusion criteria were total insulin dose ≥1.5 IU/kg/day or NPH insulin as basal.

Procedures

Participants were randomized 2:1 ([HDV-L:LIS), stratified by screening A1c (<8.5% [69 mmol/L] vs. ≥8.5%). Study medications were HDV-L (0.8 ml HDV solution in 10 ml commercial LIS) and comparator, LIS (comparably diluted with water).

Prandial dosing of HDV-lispro or control lispro was 15 minutes prior to the meal, and basal insulins were administered either as a single daily dose or a divided twice per day dosing, every 12 hours.

Informed of ~10% dilution, participants continued their current insulin parameters. Hypoglycemia was recorded on Case Report Forms (CRFs) based on subject diaries and SMBG records, subjectively investigator-judged as "mild," "moderate," "severe," or "life threatening." Blinded continuous glucose monitoring (CGM) (Dexcom G4) was used for 5-7 days to assess glucose at baseline, weeks 13 and 26. A1c, lipids, and liver enzymes were measured approximately monthly. Liver fat content MRIs were performed in a subset.

Statistical Analysis

The intent to treat (ITT) population included all randomized subjects receiving at least one dose of study treatment. Safety analyses included all randomized subjects. A sample size of 150 with assumed A1c SD of 0.8% and assumed A1c treatment difference of 0.4% had 99.9% power for non-inferiority pre-specified 0.4% margin. Mean A1c change was analyzed using ANCOVA within intent-to-treat (ITT) cohort at each visit. Post hoc subgroup analyses (baseline A1c <8.5% vs ≥8.5%) were performed, this cut point corresponding to pre-specified randomization strata. Direct likelihood models were used for treatment arm A1c comparisons, % time <54 mg/dL, bolus insulin, and basal insulin within the two A1c subgroups. Poisson regression models adjusting for site as random effect compared "severe" hypoglycemia incidence rates within A1c groups, testing for baseline A1c by treatment group interaction. Event number/subject was truncated at 15, accounting for extreme outliers.

b. Discussion

Subjects were randomly assigned HDV-L (n=118) or LIS (n=58). 62% of HDV-L patients were male, with 72% of LIS male. Mean (±SD) baseline age was 46.7±14.4 (HDV-L) and 44.1±15.7 (LIS). Mean (±SD) baseline HbA1c was 8.12±0.79 (HDV-L) and 8.22±0.90 (LIS).

Mean change in A1c baseline to Week 26 was −0.09% with (HDV-L) and −0.16% (LIS), (estimated treatment difference [ETD], HDV-L-LIS: +0.09% [95% CI −0.18 to 0.35]), confirming HDV-L non-inferiority. Analysis of hypoglycemia outcomes showed that baseline A1c status modified the treatment group effect on "severe" hypoglycemia incidence (p-value for interaction <0.001), with less hypoglycemia in HDV-L compared to LIS with poor control but higher risk in HDV-L with better control.

Further analyses were based on subgroups (A1c≥8.5% vs. <8.5%). HDV-L treated subjects with baseline A1c ≥8.5% showed a CRF-reported incidence rate of "severe" hypoglycemia significantly lower than LIS (69 vs. 97 events/100 person-years, p=0.03), and their percentage time <54 mg/dL during Week 26 (FIG. 1A) showed trend for reduction (median 0.7% vs. 2.6% for HDV-L and LIS, respectively, p=0.09). Conversely, with baseline A1c ≤8.5%, CRFs reported higher incidence of "severe" hypoglycemia with HDV-L than LIS (191 vs. 21, p=0.001), and time <54 mg/dL during Week 26 (FIG. 1B) trended higher (median 2.0% vs. 0.6%, p=0.16). No "life threatening" events were recorded.

Exploring these divergent hypoglycemia findings, insulin dosing was analyzed. Subjects with A1c ≥8.5% showed similar A1c reductions for both treatments at Week 26 (p=0.35) (FIG. 1C). However, HDV-L treated-subjects achieved A1c reductions with ~25% less bolus insulin than LIS subjects (mean 0.29 $U*kg^{-1}*day^{-1}$ vs. 0.38, respectively, p=0.02), with comparable basal doses (mean 0.38 $U*kg^{-1}*day^{-1}$ vs. 0.45, respectively, p=0.37) at study end (FIG. 1E). HDV-L and LIS subjects with baseline A1c <8.5% both showed little change in A1c over time (FIG. 1D) without difference in bolus/basal insulin dosage at endpoint (p=0.86 and 0.90 for basal and bolus, respectively) (FIG. 1F).

Lipids remained mostly stable throughout study; however, a significant reduction in total cholesterol with HDV-L (−6.5 mg/dL) vs. LIS (7.3 mg/dL) was observed (ETD: HDV-L-LIS: −12.0 mg/dL [95% CI −21.1 to −2.9, p=0.01). Liver function tests at Weeks 5 and 19 showed stable ALT/AST and bilirubin levels for both treatments. Of 21 subjects studied with MRI, 4 had measurable baseline liver fat; one subject (treated with HDV-L) showed measurable liver fat increase (3.1% baseline; 11.4% endpoint), without other evidence of hepatic dysfunction. No treatment-related serious adverse events were reported.

This is the first six-month study to demonstrate efficacy and safety of a liver-targeting rapid-acting insulin formulation in T1DM. HDV-L was non-inferior to LIS by change in A1c, with significant total cholesterol reduction and no treatment-related severe adverse events. In contrast to peglispro safety results (Jacober, et al., 2016, Diabetes Obes Metab. 18(Suppl 2):3-16), the present study showed no between-group difference in ALT.

In certain embodiments, administration of HDV-L provides more physiologic insulin distribution than free insulin administration. In other embodiments, by delivering a portion of the SC dose directly to the liver, ~30-60% of oral carbohydrate is sequestered as hepatic glycogen, reducing peripheral glucose exposure and demanding reduction in peripheral insulin exposure.

Without wishing to be limited by any theory, less well-controlled HDV-L subjects did not meaningfully alter HDV-L doses over time (whereas LIS was increased by ~25%) yet experienced less CRF-reported severe hypoglycemia and less time <54 mg/dL as compared to LIS, without difference in A1c between or within treatments. Without wishing to be limited by any theory, better-controlled HDV-L subjects failed to recognize a functional increase in insulin potency, resulting in a trend for increased time spent <54 mg/dL and significant increase in CRF-reported hypoglycemia, despite no difference in their insulin dosing or A1c outcomes. The strikingly divergent hypoglycemia risk findings and differing insulin dose adjustments observed in poor- versus better-controlled subgroups can be unified by the hypothesis that, by altering biodistribution of SC insulin to better include the liver, HDV increases the functional potency of insulin in both high- and lower-A1c subgroups.

Figure 1B:
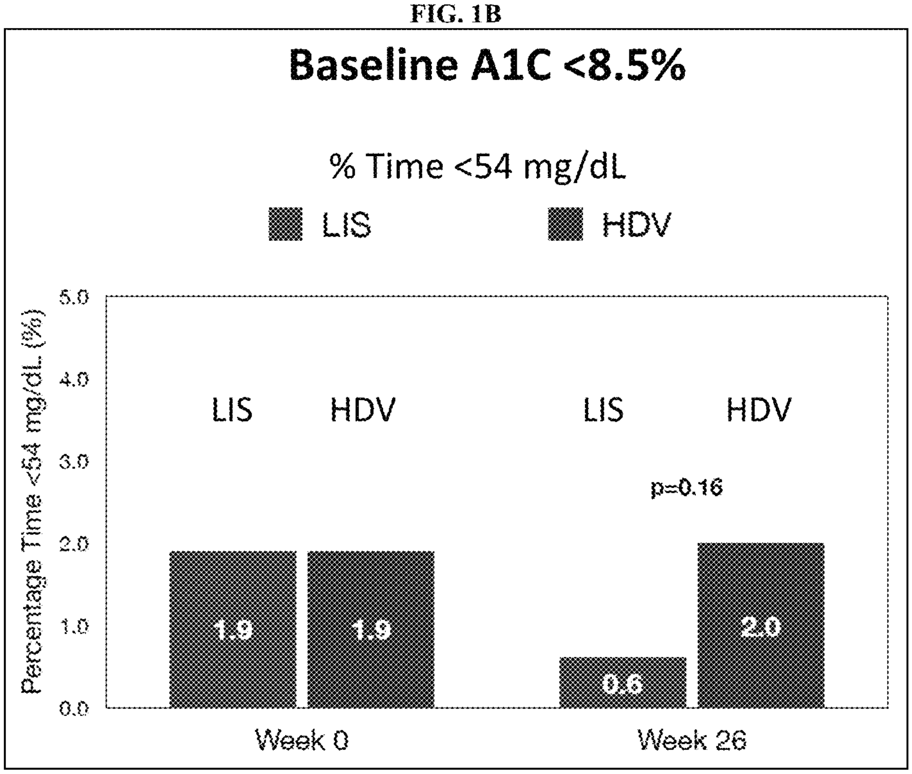
Figure 1C:
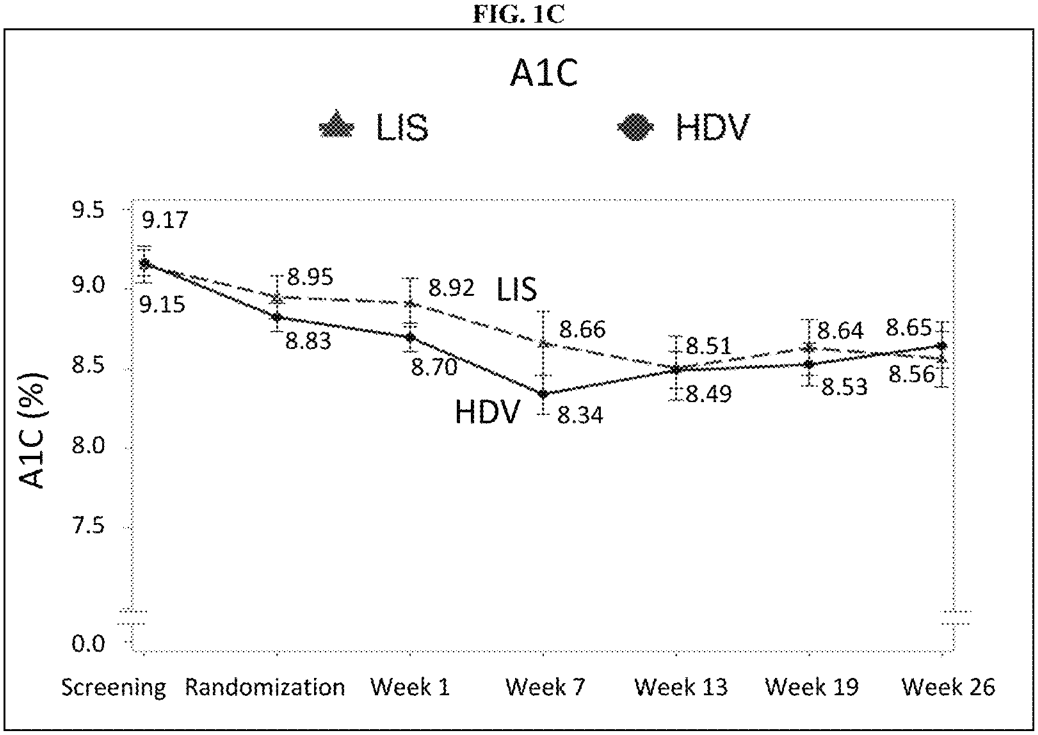
Figure 1D:
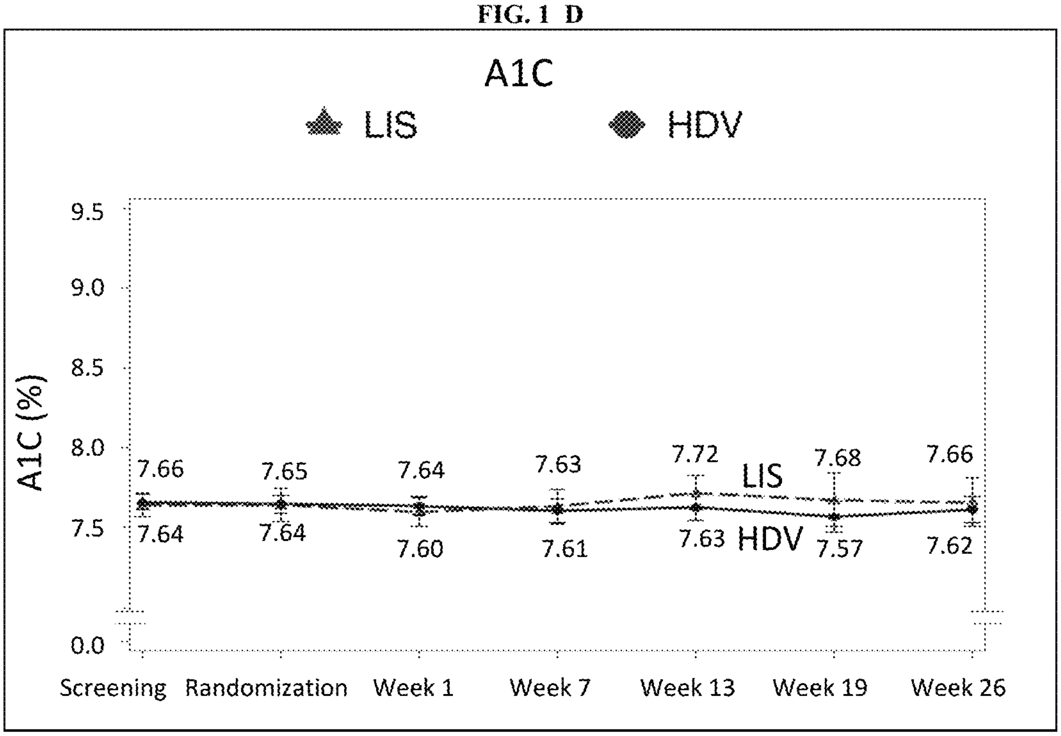
Figure 1E:
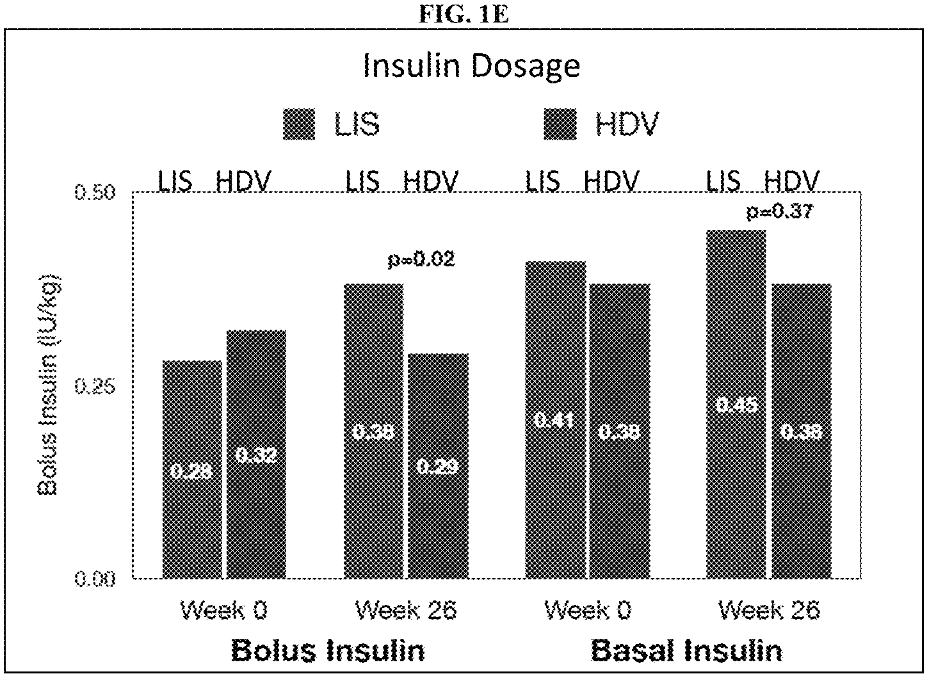
Figure 1F:
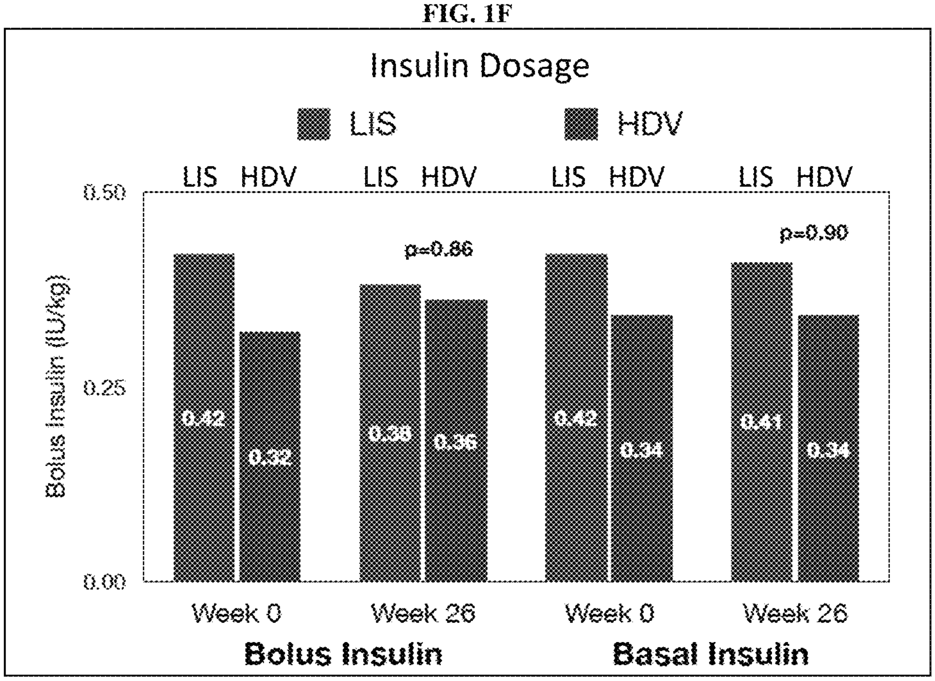

A downstream consequence of increased glycogen storage should be improved availability of hepatic glucose to counteract hypoglycemia; this may have occurred with HDV-L at baseline A1c ≥8.5%, showing both relative (compared to LIS) and absolute reductions in time below 54 mg/dL (FIG. 1A). In contrast, the lower A1c subgroup was apparently over-insulinized owing to the increased functional potency of HDV-L and lacked hyperglycemic "buffer" to limit absolute hypoglycemic risk.

The present results indicate that of HDV-L is non-inferior to LIS and its liver-targeted component potentiates insulin effect. HDV, when added to lispro insulin, distributes meal time glucose to the liver and as a result lowers peripheral blood glucose. In poorly controlled T1D subjects with HbA1c >8.5%, better glycemic control and reduced hypoglycemia was observed, even with lowered HDV-lispro insulin doses over the course of the study. However, in better controlled subjects, those with HbA1c <8.5%, the reduction in peripheral glucose load led to increased hypoglycemia incidence and severity, believed to be due to the patients not reducing their basal (non HDV) insulin dose. In certain embodiments, addition of HDV to an insulin makes the insulin appear to be more potent, necessitating a re-evaluation of the relationship of mealtime (HDV-lispro) to basal insulin dosing, which covers times of fasting, especially overnight.

Example 2: Pump Study

A study was run comparing the efficacy of HDV lispro vs. lispro to treat adult Type 1 diabetes mellitus when administered by pump. The study involved 7 subjects and was a randomized, double-blinded two-way crossover study. The dosing duration was 3-week on standard insulin×3-week on HDV-insulin with infusion via standard commercial insulin pumps, and a mixed meal test was employed; continuous glucose monitoring was achieved via blinded Dexcom G4 Platinum Continuous Glucose Monitor. The baseline HbA1c was 7.19, and the ending HbA1c was 7.21 (for the HDV group) and 7.08 (for the lispro group).

Figure 2A:
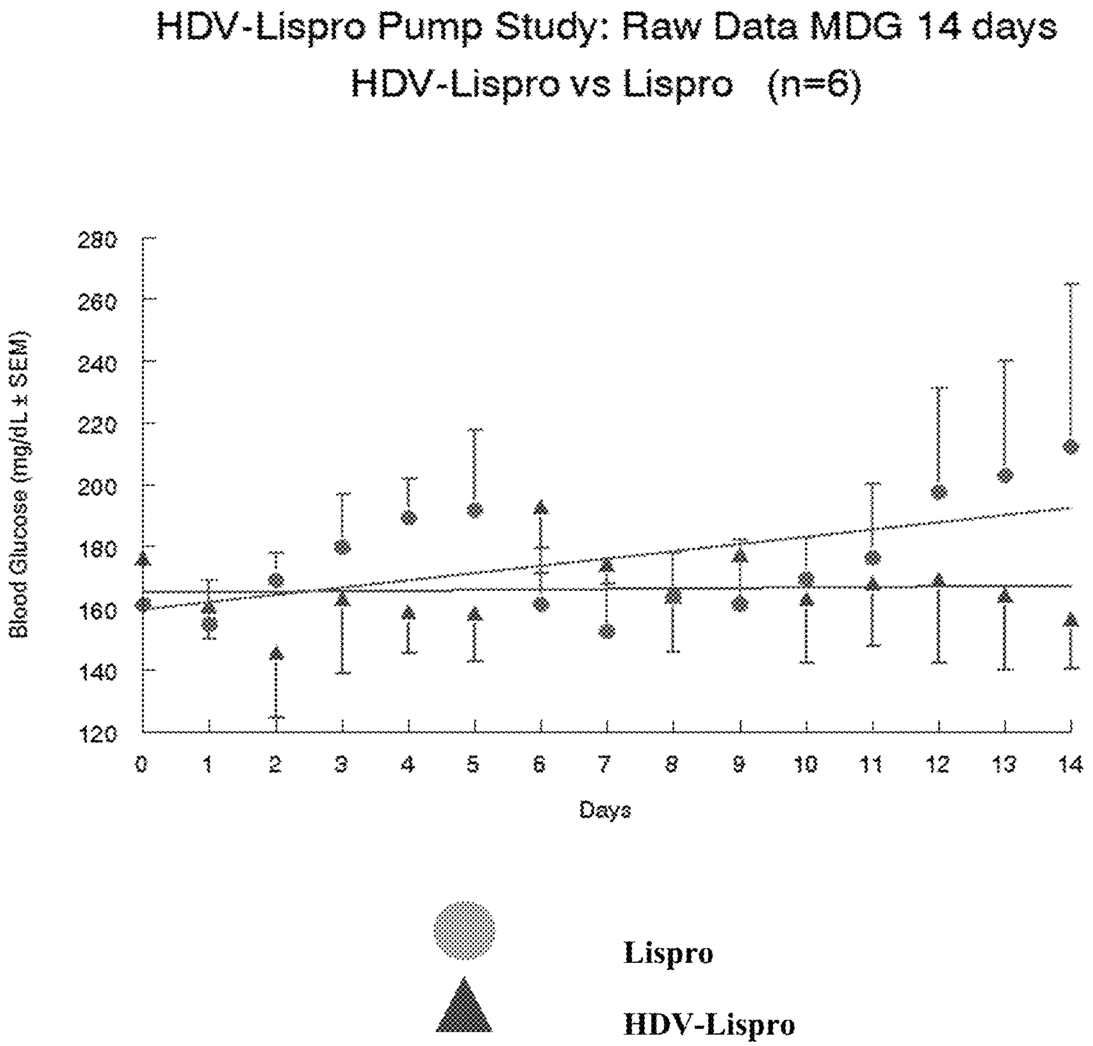
FIGS. 2A-2C illustrate results for the insulin pump study described in Example 2.
Figure 2B:
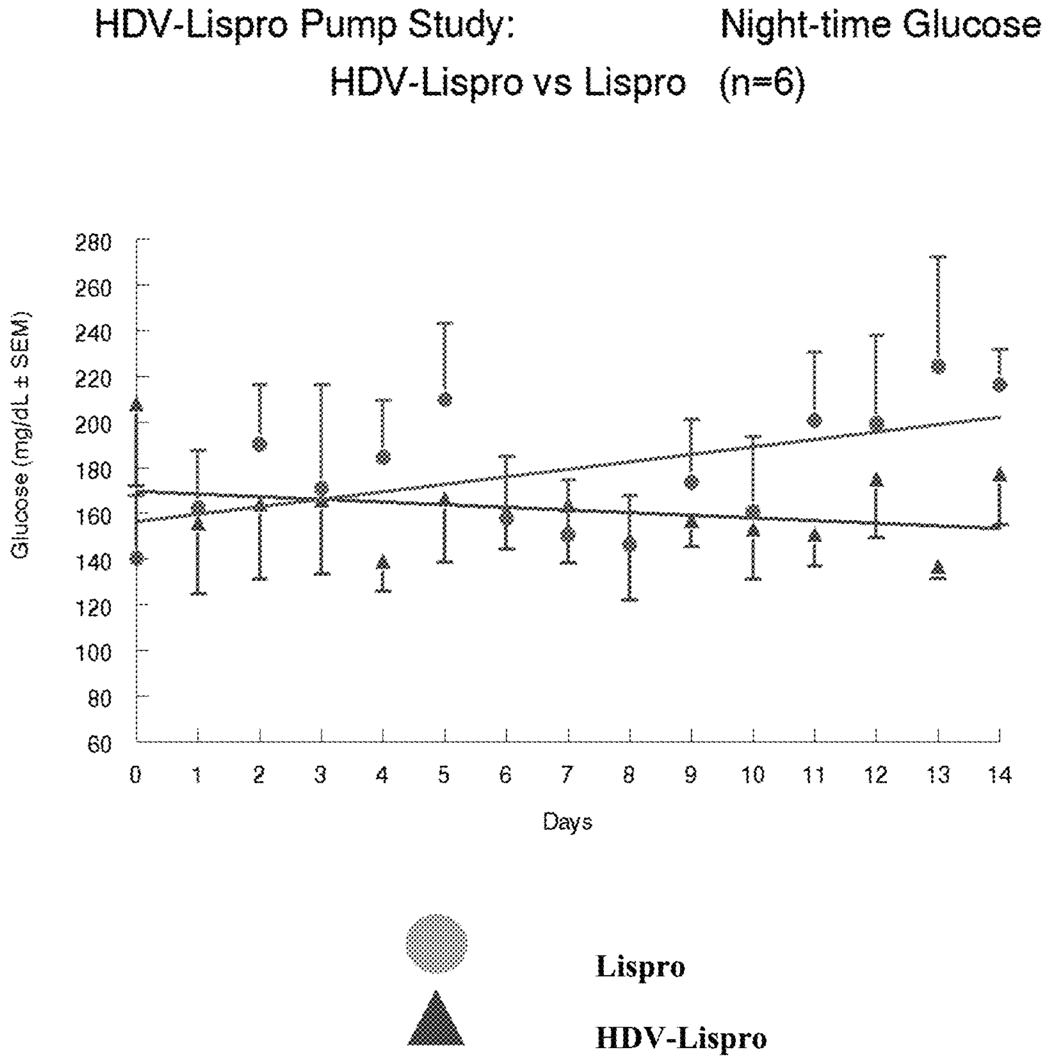
Figure 2C:
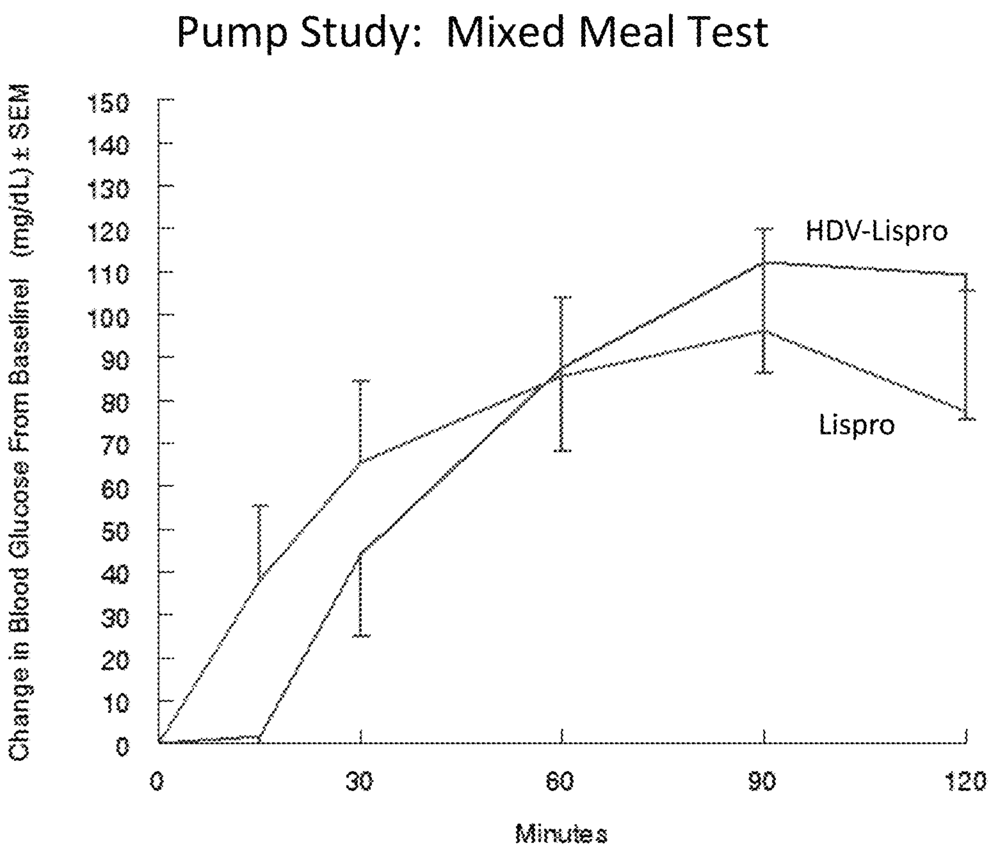

Mean daily glucose values (absolute values over two weeks) are illustrated in FIG. 2A. Two-week absolute change in mean nighttime glucose (mg/dL) is illustrated in FIG. 2B. FIG. 2C illustrates mixed meal tolerance test changes from baseline blood glucose. The study showed a decrease in mean daily and mean night time blood glucose levels upon use of HDV-insulin in the pump.

The study indicates that HDV-insulin achieves better results in lowering mean daily blood glucose levels and mean nighttime blood glucose levels, as compared to control insulin that was not formulated with HDV (see FIG. 2B, for example). In certain embodiments, such result is obtained without changing the total levels of insulin over a 24-hour time period, as compared to control insulin that did not have HDV (free insulin). In other embodiments, such result is obtained using lower total levels of insulin over a 24-hour time period, as compared to control insulin that did not have HDV (free insulin). In yet other embodiments, the continuous administration of HDV-insulin to the subject allows for superior glucose control in the overnight period (basal glucose control).

Example 3

A double-blinded, randomized study was run comparing the efficacy of HDV lispro vs. lispro to treat adult Type 1 diabetes mellitus. The study involved 43 (1:1) subjects (who were considered to be in good control, with HbA1c levels between 7-8%) and was a six-week parallel design study, with multiple daily injections. The baseline HbA1c was 7.35 (HDV group) and 7.39 (lispro group). The primary endpoint was a two-hour reduction in glucose time out of range.

Figure 3A:
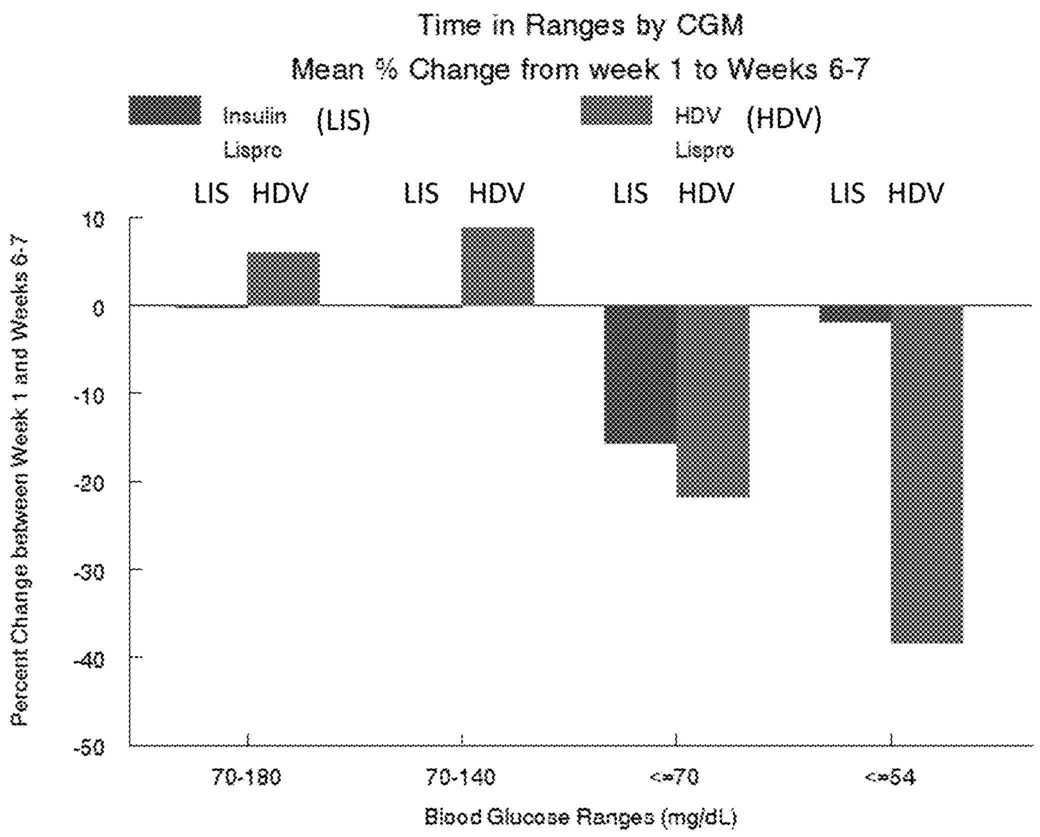
FIGS. 3A-3C illustrate results for the study described in Example 3.
Figure 3B:
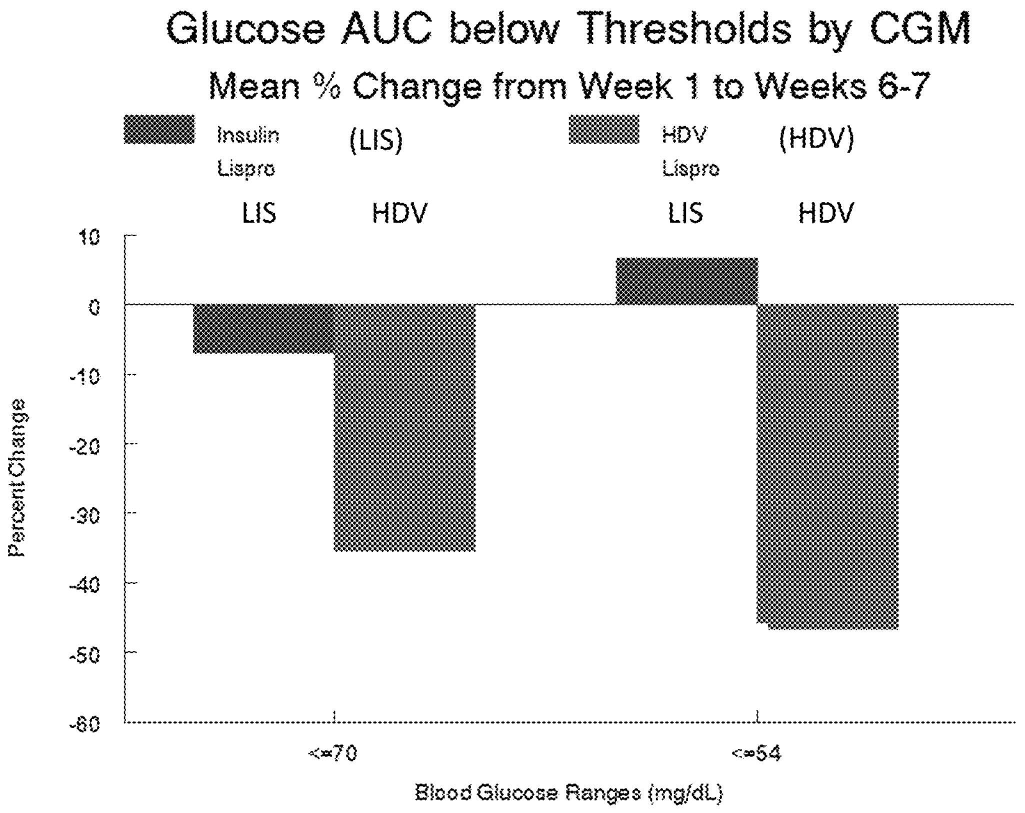
Figure 3C:
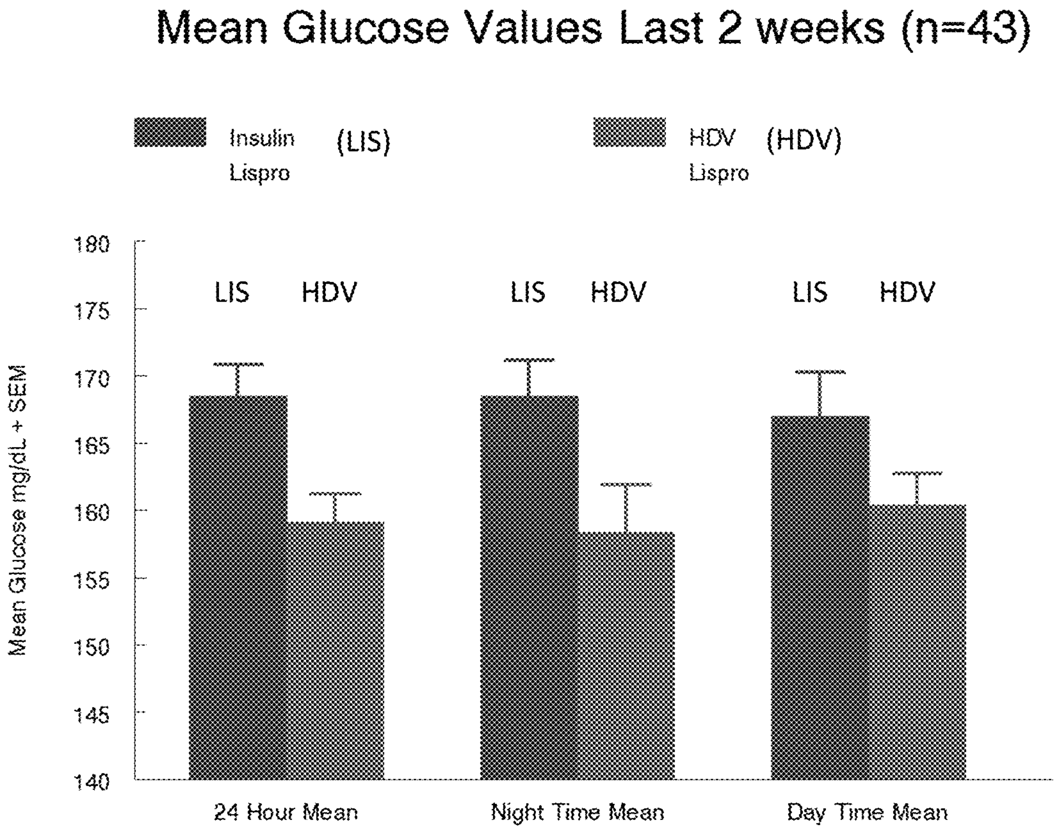
Figure 4:
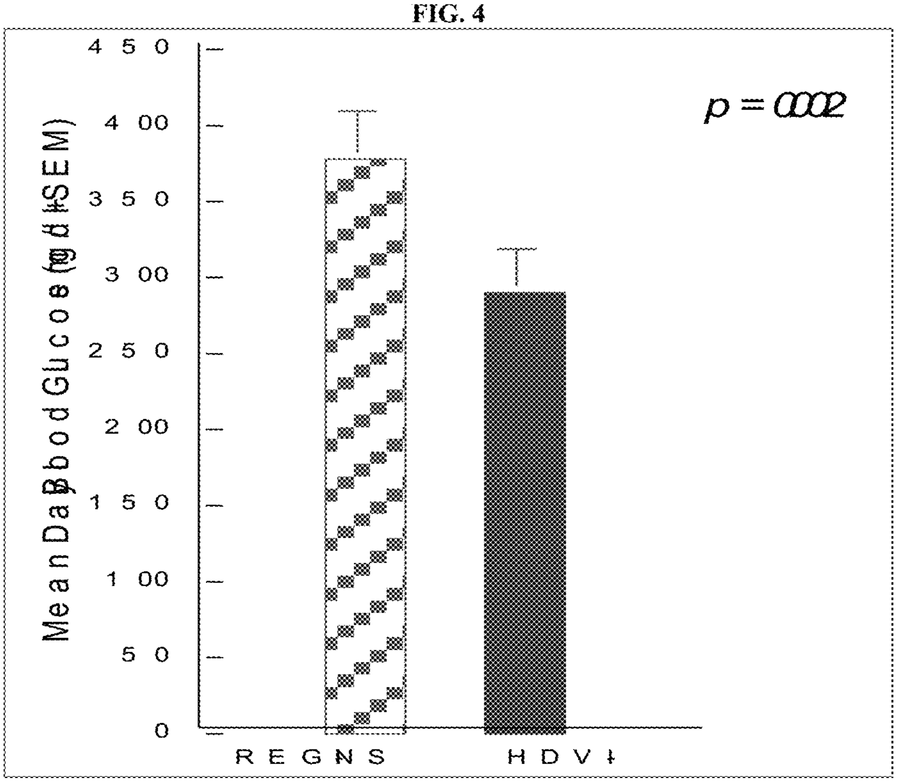
FIG. 4 comprises a graph illustrating results of a six-week dog study in insulin-deficient dogs, where mean daily blood glucose was measured. This graph shows a reduction in mean daily glucose in the dogs. The study also showed a dramatic reduction in hypoglycemia in the dogs.
Figure 5:
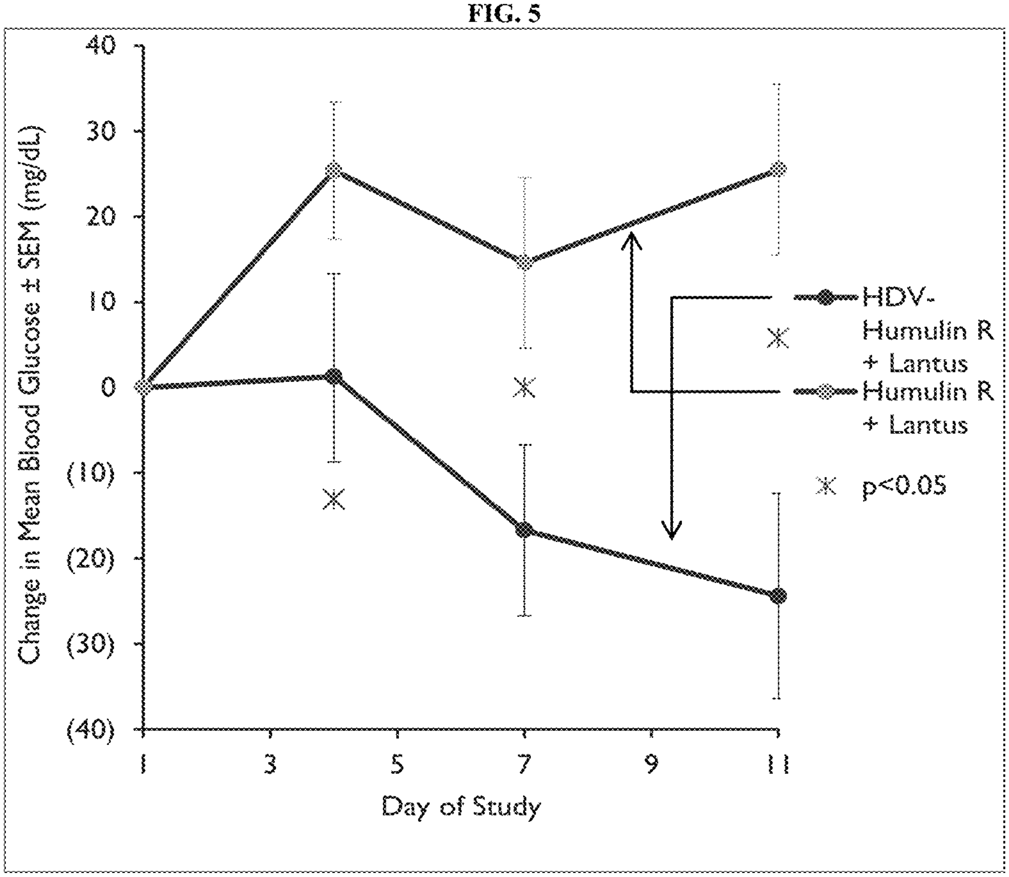
FIG. 5 comprises a graph illustrating results for a human T1D study in 20 human subjects. This randomized, double blind study was run for two weeks, wherein half the subjects received standard insulin treatment and the rest had standard treatment plus HDV insulin at meal times. The HDV treatment resulted in a dramatic reduction in mean daily glucose.

FIG. 3A illustrates time in ranges by continuous glucose monitoring (CGM), in term sof mean % change from week 1 to weeks 6-7. FIG. 3B illustrates HDV lispro effect on hypoglycemia, in terms of mean % change in glucose AUC below 70 mg/dL and 54 mg/dL. FIG. 3C illustrates differences in mean blood glucose values during weeks 6-7. The results show a reduction in mean daily glucose and a trend to less frequent and severe hypoglycemia, which means overall better control of diabetes mellitus.

Table 1 illustrates effects of HDV on time in range and time in target for Examples 2-3.

TABLE 1

| | Example 2 | Example 3 |
|---|---|---|
| Time in Range (70-180 mg/dL) | 1 hour increase | 0.78 hour increase* |
| Time in Target (70-140 mg/dL) | 1.5 hour increase | 0.72 hour increase* |
| Time <54 mg/dL | 40% decrease | 38% decrease** |
| Area <54 mg/dL | 39% decrease | 47% decrease*** |
| Time ≤70 mg/dL | 24% decrease | 22% decrease**** |
| Area ≤70 mg/dL | 34% decrease | 35% decrease***** |
| Glucose ACU (MMTT) | 30% decrease (1 hour; 75 g CHO) | 33.5% decrease (0-5 hr; 100 g CHO) |

*No Change in Lispro Group
**2% increase in Lispro Group
***7% increase in Lispro Group
****16% decrease in Lispro Group
*****7% increase in Lispro Group The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of improving blood glucose control in a human subject suffering from diabetes mellitus, the method comprising:

selecting a human subject suffering from diabetes mellitus with a baseline HbA1c value who had been administered a baseline diabetes treatment comprising a baseline free bolus insulin formulated in the absence of a hepatic delivery vehicle (HDV) and a baseline free basal insulin;

administering to the human subject (a) instead of the baseline free bolus insulin, a HDV bolus insulin composition comprising insulin and a lipid-based nanoparticle, wherein the insulin is dispersed within the nanoparticle, and (b) a free basal insulin;

wherein one of the following applies:

(a) if the human subject has a baseline HbA1c value greater than 8.5%, then the human subject is administered a HDV bolus insulin composition with an insulin amount lower than the amount of baseline free bolus insulin and the human subject is administered a free basal insulin amount that is about the same as the baseline free basal insulin;

(b) if the human subject has a baseline HbA1c value between 7% and 8.5%, then the human subject is administered a HDV bolus insulin composition with an insulin amount that is about equal to the baseline free bolus insulin and the human subject is administered a free basal insulin amount that is lower than the baseline free basal insulin;

wherein the administering results in better blood glucose control as compared to the baseline diabetes treatment;

wherein the administering further results in at least one of the following:

(i) no significant hypoglycemia in the human subject;

(ii) no significant iatrogenic hyperinsulinemia in the human subject;

wherein the nanoparticle is enclosed by a bipolar lipid membrane comprising cholesterol, dicetyl phosphate, an amphipathic lipid, and a hepatocyte receptor binding molecule;

wherein the amphipathic lipid comprises at least one selected from the group consisting of 1,2-distearoyl-sn-glycero-3-phosphocholine, 1,2-dipalmitoyl-sn-glycerol-[3-phospho-rac-(1-glycerol)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine;

wherein the at least one hepatocyte receptor binding molecule extends outward from the nanoparticle; and wherein the size of the nanoparticle ranges from about 10 nm to about 150 nm.

2. A method of improving blood glucose control in a human subject suffering from diabetes mellitus, the method comprising:

selecting a human subject suffering from diabetes mellitus with a baseline HbA1c value who had been administered a baseline treatment comprising a continuous administration of a baseline free insulin formulated in the absence of a hepatic delivery vehicle (HDV);

administering to the human subject in a continuous manner, instead of the baseline free insulin, a HDV composition comprising insulin and a lipid-based nanoparticle, wherein the insulin is dispersed within the nanoparticle;

wherein the amount of the insulin in the HDV composition is lower than the amount of the baseline free insulin;

wherein the administering results in better blood glucose control as afforded by the baseline treatment;

wherein the nanoparticle is enclosed by a bipolar lipid membrane comprising cholesterol, dicetyl phosphate, an amphipathic lipid, and a hepatocyte receptor binding molecule;

wherein the amphipathic lipid comprises at least one selected from the group consisting of 1,2-distearoyl-sn-glycero-3-phosphocholine, 1,2-dipalmitoyl-sn-glycerol-[3-phospho-rac-(1-glycerol)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine;

wherein the at least one hepatocyte receptor binding molecule extends outward from the nanoparticle; and wherein the size of the nanoparticle ranges from about 10 nm to about 150 nm.

3. The method of claim 2, wherein the HDV composition is administered continuously to the human subject over a period of at least 24 hours, or wherein the HDV composition is administered continuously to the human subject using a pump.

4. The method of claim 1, wherein the bipolar lipid membrane further comprises at least one agent selected from the group consisting of a stabilizer and stearoyl lysophosphatidylcholine.

5. The method of claim 4, wherein the stabilizer is selected from the group consisting of m-cresol, benzyl alcohol, methyl 4-hydroxybenzoate, thiomersal, and butylated hydroxytoluene (2,6-di-tert-butyl-4-methylphenol).

6. The method of claim 4, wherein the stabilizer ranges from about 10% to about 25% (w/w) in the bipolar lipid membrane.

7. The method of claim 4, wherein the stearoyl lysophosphatidylcholine ranges from about 5% to about 30% (w/w) in the bipolar lipid membrane.

8. The method of claim 1, wherein the insulin is covalently bound to the nanoparticle or wherein the insulin is not covalently bound to the nanoparticle.

9. The method of claim 1, wherein in the HDV bolus insulin composition the insulin is suspended in an aqueous solution comprising a free dissolved insulin that is not dispersed within the nanoparticle.

10. The method of claim 9, wherein the free basal insulin, the nanoparticle-dispersed insulin, and the free dissolved insulin are independently selected from the group consisting of insulin lispro, insulin aspart, regular insulin, insulin glargine, insulin zinc, extended human insulin zinc suspension, isophane insulin, human buffered regular insulin, insulin glulisine, recombinant human regular insulin, recombinant human insulin isophane, and any combinations thereof.

11. The method of claim 1, wherein the amphipathic lipid comprises at least one selected from the group consisting of 1,2-distearoyl-sn-glycero-3-phosphocholine, 1,2-dipalmitoyl-sn-glycero-3-phosphocholine, 1,2-dipalmitoyl-sn-glycero-3-[phospho-rac-(1-glycerol)], 1,2-distearoyl-sn-glycero-3-phosphoethanolamine, and 1,2-dipalmitoyl-sn-glycero-3-phosphoethanolamine-N-(succinyl).

12. The method of claim 1, wherein the hepatocyte receptor binding molecule comprises biotin.

13. The method of claim 12, wherein the biotin-containing hepatocyte receptor binding molecule comprises at least one selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE (2,3-diacetoxypropyl 2-(5-((3aS,6aR)-2-oxohexahydro-1H-thieno[3,4-d]imidazol-4-yl) pentanamido) ethyl phosphate); biotin-X-DHPE (2,3-diacetoxypropyl 2-(6-(5-((3aS,6aR)-2-oxohexahydro-1H-thieno[3,4-d]imidazol-4-yl) pentanamido) hexanamido) ethyl phosphate); 12-((biotinyl) amino) dodecanoic acid; 12-((biotinyl) amino) dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC) biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl) biocytin; ARP; biotin-1-sulfoxide; biotin methyl ester; biotin-maleimide; biotin-poly(ethyleneglycol) amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide;

Biotin-Lewis-Y tetrasaccharide; Biotin-α-D-mannopyranoside; and biotin 6-O-phospho-α-D-mannopyranoside.

14. The method of claim 12, wherein the biotin-containing hepatocyte receptor binding molecule comprises at least one selected from the group consisting of biotin DHPE and biotin-X-DHPE.

15. The method of claim 1, wherein the composition further comprises cellulose acetate phthalate, which is at least partially bound to the insulin dispersed within the nanoparticle, or wherein the composition further comprises at least one charged organic molecule bound to the insulin dispersed within the nanoparticle, wherein the charged organic molecule is at least one selected from the group consisting of protamines, polylysine, poly(arg-pro-thr)$_n$ in a mole ratio of 1:1:1, poly(DL-Ala-poly-L-lys)$_n$ in a mole ratio of 6:1, histones, sugar polymers comprising a primary amino group, polynucleotides with primary amino groups, proteins comprising amino acid residues with carboxyl ($COO^-$) or sulfhydral ($S^-$) functional groups, and acidic polymers.

16. The method of claim 4, wherein at least one applies:

(a) the cholesterol ranges from about 5% to about 25% (w/w) in the bipolar lipid membrane;

(b) the dicetyl phosphate ranges from about 10% to about 25% (w/w) in the bipolar lipid membrane;

(c) the DSPC ranges from about 40% to about 75% (w/w) in the bipolar lipid membrane;

(d) the hepatocyte receptor binding molecule ranges from about 0.5% to about 10% (w/w) in the bipolar lipid membrane;

(e) the amount of the stearoyl lysophosphatidylcholine in the bipolar lipid membrane is about 5%-30% (w/w) of the amount of DSPC in the bipolar lipid membrane.

17. The method of claim 4, wherein the bipolar lipid membrane comprises one of the following:

(a) cholesterol, dicetyl phosphate, DSPC, stearoyl lysophosphatidylcholine, m-cresol, and at least one selected from the group consisting of biotin DHPE and biotin-X-DHPE;

(b) cholesterol, dicetyl phosphate, DSPC, m-cresol, and at least one selected from the group consisting of biotin DHPE and biotin-X-DHPE; and (c) cholesterol, dicetyl phosphate, DSPC, stearoyl lysophosphatidylcholine, and at least one selected from the group consisting of biotin DHPE and biotin-X-DHPE.

18. The method of claim 1, wherein the human subject has Type 1 diabetes or Type 2 diabetes.

19. The method of claim 2, wherein the bipolar lipid membrane further comprises at least one agent selected from the group consisting of a stabilizer and stearoyl lysophosphatidylcholine.

20. The method of claim 19, wherein the stabilizer is selected from the group consisting of m-cresol, benzyl alcohol, methyl 4-hydroxybenzoate, thiomersal, and butylated hydroxytoluene (2,6-di-tert-butyl-4-methylphenol).

21. The method of claim 19, wherein the stabilizer ranges from about 10% to about 25% (w/w) in the bipolar lipid membrane.

22. The method of claim 19, wherein the stearoyl lysophosphatidylcholine ranges from about 5% to about 30% (w/w) in the bipolar lipid membrane.

23. The method of claim 2, wherein the insulin is covalently bound to the nanoparticle or wherein the insulin is not covalently bound to the nanoparticle.

24. The method of claim 2, wherein in the HDV bolus insulin composition the insulin is suspended in an aqueous solution comprising a free dissolved insulin that is not dispersed within the nanoparticle.

25. The method of claim 24, wherein the free basal insulin, the nanoparticle-dispersed insulin, and the free dissolved insulin are independently selected from the group consisting of insulin lispro, insulin aspart, regular insulin, insulin glargine, insulin zinc, extended human insulin zinc suspension, isophane insulin, human buffered regular insulin, insulin glulisine, recombinant human regular insulin, recombinant human insulin isophane, and any combinations thereof.

26. The method of claim 2, wherein the amphipathic lipid comprises at least one selected from the group consisting of 1,2-distearoyl-sn-glycero-3-phosphocholine, 1,2-dipalmitoyl-sn-glycero-3-phosphocholine, 1,2-dipalmitoyl-sn-glycero-3-[phospho-rac-(1-glycerol)], 1,2-distearoyl-sn-glycero-3-phosphoethanolamine, and 1,2-dipalmitoyl-sn-glycero-3-phosphoethanolamine-N-(succinyl).

27. The method of claim 2, wherein the hepatocyte receptor binding molecule comprises biotin.

28. The method of claim 27, wherein the biotin-containing hepatocyte receptor binding molecule comprises at least one selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE (2,3-diacetoxypropyl 2-(5-((3aS,6aR)-2-oxohexahydro-1H-thieno[3,4-d]imidazol-4-yl) pentanamido) ethyl phosphate); biotin-X-DHPE (2,3-diacetoxypropyl 2-(6-(5-((3aS,6aR)-2-oxohexahydro-1H-thieno[3,4-d]imidazol-4-yl) pentanamido) hexanamido) ethyl phosphate); 12-((biotinyl) amino) dodecanoic acid; 12-((biotinyl) amino) dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC) biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl) biocytin; ARP; biotin-1-sulfoxide; biotin methyl ester; biotin-maleimide; biotin-poly(ethyleneglycol) amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; and biotin 6-O-phospho-α-D-mannopyranoside.

29. The method of claim 27, wherein the biotin-containing hepatocyte receptor binding molecule comprises at least one selected from the group consisting of biotin DHPE and biotin-X-DHPE.

30. The method of claim 2, wherein the composition further comprises cellulose acetate phthalate, which is at least partially bound to the insulin dispersed within the nanoparticle, or wherein the composition further comprises at least one charged organic molecule bound to the insulin dispersed within the nanoparticle, wherein the charged organic molecule is at least one selected from the group consisting of protamines, polylysine, poly(arg-pro-thr)$_n$ in a mole ratio of 1:1:1, poly(DL-Ala-poly-L-lys)$_n$ in a mole ratio of 6:1, histones, sugar polymers comprising a primary amino group, polynucleotides with primary amino groups, proteins comprising amino acid residues with carboxyl ($COO^-$) or sulfhydral($S^-$) functional groups, and acidic polymers.

31. The method of claim 19, wherein at least one applies:

(a) the cholesterol ranges from about 5% to about 25% (w/w) in the bipolar lipid membrane;

(b) the dicetyl phosphate ranges from about 10% to about 25% (w/w) in the bipolar lipid membrane;

(c) the DSPC ranges from about 40% to about 75% (w/w) in the bipolar lipid membrane;

(d) the hepatocyte receptor binding molecule ranges from about 0.5% to about 10% (w/w) in the bipolar lipid membrane;

(e) the amount of the stearoyl lysophosphatidylcholine in the bipolar lipid membrane is about 5%-30% (w/w) of the amount of DSPC in the bipolar lipid membrane.

32. The method of claim 19, wherein the bipolar lipid membrane comprises one of the following:

(a) cholesterol, dicetyl phosphate, DSPC, stearoyl lysophosphatidylcholine, m-cresol, and at least one selected from the group consisting of biotin DHPE and biotin-X-DHPE;

(b) cholesterol, dicetyl phosphate, DSPC, m-cresol, and at least one selected from the group consisting of biotin DHPE and biotin-X-DHPE; and (c) cholesterol, dicetyl phosphate, DSPC, stearoyl lysophosphatidylcholine, and at least one selected from the group consisting of biotin DHPE and biotin-X-DHPE.

33. The method of claim 2, wherein the human subject has Type 1 diabetes or Type 2 diabetes.

* * * * *